United States Patent [19]
Ghadiri

[11] Patent Number: 5,200,504
[45] Date of Patent: Apr. 6, 1993

[54] METALLOPEPTIDES HAVING STABILIZED SECONDARY STRUCTURES

[75] Inventor: Reza M. Ghadiri, Del Mar, Calif.

[73] Assignee: The Scripps Research Institute, La Jolla, Calif.

[21] Appl. No.: 591,988

[22] Filed: Oct. 2, 1990

[51] Int. Cl.[5] ............... A61K 37/02; A61K 37/26; C07K 5/00; C07K 7/00
[52] U.S. Cl. .................. 530/304; 530/326; 530/300; 530/325
[58] Field of Search ............... 530/326, 300, 325, 304

[56] References Cited
U.S. PATENT DOCUMENTS
4,849,505 7/1989 Stavrianopoulos ............. 530/300

OTHER PUBLICATIONS
Kemp et al., Tetrahedron Lett., vol. 29, pp. 4931–4934, 1988.
Ghadiri et al., J. Am. Chem. Soc., vol. 112, pp. 9633–9635, 1990.
Ghadiri et al., J. Am. Chem. Soc. 112: 1630–1632 (1990).
Ghadiri, et al., J. Am. Chem. Soc. 112; 9633–9635 (1990).

Primary Examiner—Merrell C. Cashion, Jr.
Assistant Examiner—A. M. Davenport
Attorney, Agent, or Firm—Douglas A. Bingham; Thomas Fitting; April C. Logan

[57] ABSTRACT

The invention contemplates a metallopeptide and a method for producing the metallopeptide. The metallopeptide comprises a polypeptide bonded to a metal cation at two coordinating amino acid residues that are aqueous solvent-accessible, said metallopeptide having a secondary structure stabilized by said bonded metal cation.

15 Claims, 5 Drawing Sheets

Ac-Ala-Glu-Ala-Ala-Ala-Lys-Glu-Ala-Ala-Ala-Lys-$X_1$-Ala-Ala-Ala-$X_2$-Ala-NH$_2$
Peptide 1, $X_1$=Cys, $X_2$=His
Peptide 2, $X_1$=$X_2$=His Ac-Ala-Glu-Ala-Ala-Ala-Lys-Glu-Ala-Ala-Ala-Ala-Lys-X₁-Ala-Ala-Ala-Ala-X₂-Ala-NH₂
Peptide 1, X₁=Cys, X₂=His
Peptide 2, X₁=X₂=His

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=Ac
/ note="Ac represents an acetylated amino terminus"

( i x ) FEATURE:
( A ) NAME/KEY: Binding-site
( B ) LOCATION: 12
( D ) OTHER INFORMATION: /note="Metal ligand coordinating contact site"

( i x ) FEATURE:
( A ) NAME/KEY: Binding-site
( B ) LOCATION: 16
( D ) OTHER INFORMATION: /note="Metal ligand coordinating contact site"

( i x ) FEATURE:
( A ) NAME/KEY: Modified-site
( B ) LOCATION: 17
( D ) OTHER INFORMATION: /label=CONH2
/ note="CONH2 represents an amidated carboxyl terminus"

( x i ) SEQUENCE DESCRIPTION: SEQ ID NO:1:

Ala Glu Ala Ala Ala Lys Glu Ala Ala Ala Lys Cys Ala Ala Ala His
1               5                   10                  15
Ala ( 2 ) INFORMATION FOR SEQ ID NO:2:

( i ) SEQUENCE CHARACTERISTICS:
( A ) LENGTH: 17 amino acids
( B ) TYPE: amino acid
( C ) STRANDEDNESS: single
( D ) TOPOLOGY: linear (i i) MOLECULE TYPE: peptide (i x) FEATURE:
    (A) NAME/KEY: Modified-site
    (B) LOCATION: 1
    (D) OTHER INFORMATION: /label=Ac
    / note="Ac represents an acetylated amino terminus"

(i x) FEATURE:
    (A) NAME/KEY: Binding-site
    (B) LOCATION: 12
    (D) OTHER INFORMATION: /note="Metal ligand coordinating contact site"

(i x) FEATURE:
    (A) NAME/KEY: Binding-site
    (B) LOCATION: 16
    (D) OTHER INFORMATION: /note="Metal ligand coordinating contact site"

(i x) FEATURE:
    (A) NAME/KEY: Modified-site
    (B) LOCATION: 17
    (D) OTHER INFORMATION: /label=CONH2
    / note="COHN2 represents an amidated carboxyl terminus"

(x i) SEQUENCE DESCRIPTION: SEQ ID NO:2:

Ala Glu Ala Ala Ala Lys Glu Ala Ala Ala Lys His Ala Ala Ala His
1             5                    10                 15

Ala (2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /label=Ac
        / note="Ac represents an acetylated amino terminus"

(i x) FEATURE:
        (A) NAME/KEY: Binding-site
        (B) LOCATION: 7
        (D) OTHER INFORMATION: /note="Metal ligand coordinating contact site"

(i x) FEATURE:
        (A) NAME/KEY: Binding-site
        (B) LOCATION: 11
        (D) OTHER INFORMATION: /note="Metal ligand coordinating contact site"

(i x) FEATURE:
        (A) NAME/KEY: Modified-site
        (B) LOCATION: 17
        (D) OTHER INFORMATION: /label=CONH2
        / note="CONH2 represents an amidated carboxyl terminus"

(x i) SEQUENCE DESCRIPTION: SEQ ID NO:3:

Ala Glu Ala Ala Ala Lys His Ala Ala Ala His Glu Ala Ala Ala Lys
1             5                    10                 15

Ala (2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
        / note="Ac represents an acetylated amino terminus"

( i x ) FEATURE:
        ( A ) NAME/KEY: Binding-site
        ( B ) LOCATION: 12
        ( D ) OTHER INFORMATION: /note="Metal ligand coordinating contact site"

( i x ) FEATURE:
        ( A ) NAME/KEY: Binding-site
        ( B ) LOCATION: 16
        ( D ) OTHER INFORMATION: /note="Metal ligand coordinating contact site"

( i x ) FEATURE:
        ( A ) NAME/KEY: Modified-site
        ( B ) LOCATION: 17
        ( D ) OTHER INFORMATION: /label=CONH2
        / note="CONH2 represents an amidated carboxy; terminus"

( x i ) SEQUENCE DESCRIPTION: SEQ ID NO:4:

Ala Glu Ala Ala Ala Lys Glu Ala Ala Ala Lys His Ala Ala Ala His
1               5                       10                  15

Ala ( 2 ) INFORMATION FOR SEQ ID NO:5:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
        / note="Ac represents an acetylated amino terminus"

( i x ) FEATURE:
        ( A ) NAME/KEY: Binding-site
        ( B ) LOCATION: 7
        ( D ) OTHER INFORMATION: /note="Metal ligand coordinating contact site"

( i x ) FEATURE:
        ( A ) NAME/KEY: Binding-site
        ( B ) LOCATION: 11
        ( D ) OTHER INFORMATION: /note="Metal ligand coordinating contact site"

( i x ) FEATURE:
        ( A ) NAME/KEY: Modified-site
        ( B ) LOCATION: 17
        ( D ) OTHER INFORMATION: /label=CONH2
        / note="CONH2 represents an amidated carboxyl terminus"

( x i ) SEQUENCE DESCRIPTION: SEQ ID NO:5:

Ala Glu Ala Ala Ala Lys His Ala Ala Ala His Glu Ala Ala Ala Lys
1               5                       10                  15

Ala ( 2 ) INFORMATION FOR SEQ ID NO:6:

( i ) SEQUENCE CHARACTERISTICS:
        ( A ) LENGTH: 17 amino acids
        ( B ) TYPE: amino acid ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /label=Ac
        / note="Ac represents an acetylated
                                        amino terminus"

( i x ) FEATURE:
            ( A ) NAME/KEY: Binding-site
            ( B ) LOCATION: 2
            ( D ) OTHER INFORMATION: /note="Metal ligand coordinating
                                        contact site"

( i x ) FEATURE:
            ( A ) NAME/KEY: Binding-site
            ( B ) LOCATION: 6
            ( D ) OTHER INFORMATION: /note="Metal ligand coordinating
                                        contact site"

( i x ) FEATURE:
            ( A ) NAME/KEY: Modified-site
            ( B ) LOCATION: 17
            ( D ) OTHER INFORMATION: /label=CONH2
                                    / note="CONH2 represents an amidated
                                        carboxyl terminus"

( x i ) SEQUENCE DESCRIPTION: SEQ ID NO:6:

Ala His Ala Ala Ala His Glu Ala Ala Ala Lys Glu Ala Ala Ala Lys
    1               5                   10                  15

Ala ( 2 ) INFORMATION FOR SEQ ID NO:7:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /label=Ac
                                    / note="Ac represents an acetylated
                                        amino terminus"

( i x ) FEATURE:
            ( A ) NAME/KEY: Binding-site
            ( B ) LOCATION: 2
            ( D ) OTHER INFORMATION: /note="Metal ligand coordinating
                                        contact site"

( i x ) FEATURE:
            ( A ) NAME/KEY: Binding-site
            ( B ) LOCATION: 6
            ( D ) OTHER INFORMATION: /note="Metal ligand coordinating
                                        contact site"

( i x ) FEATURE:
            ( A ) NAME/KEY: Modified-site
            ( B ) LOCATION: 17
            ( D ) OTHER INFORMATION: /label=CONH2
                                    / note="CONH2 represents an amidated
                                        carboxyl terminus"

( x i ) SEQUENCE DESCRIPTION: SEQ ID NO:7:

Ala Cys Ala Ala Ala His Glu Ala Ala Ala Lys Glu Ala Ala Ala Lys
    1               5                   10                  15

Ala ( 2 ) INFORMATION FOR SEQ ID NO:8:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
        / note="Ac represents an acetylated amino terminus"

( i x ) FEATURE:
        ( A ) NAME/KEY: Binding-site
        ( B ) LOCATION: 3
        ( D ) OTHER INFORMATION: /note="Metal ligand coordinating contact site"

( i x ) FEATURE:
        ( A ) NAME/KEY: Binding-site
        ( B ) LOCATION: 7
        ( D ) OTHER INFORMATION: /note="Metal ligand coordinating contact site"

( i x ) FEATURE:
        ( A ) NAME/KEY: Modified-site
        ( B ) LOCATION: 19
        ( D ) OTHER INFORMATION: /label=CONH2
        / note="CONH2 represents an amidated carboxyl terminus"

( x i ) SEQUENCE DESCRIPTION: SEQ ID NO:8:

Ala Ala His Ala Leu Glu His Gln Ala Lys Ala Leu Lys Glu Ala Ala
1               5                   10                  15

Gln Lys Ala ( 2 ) INFORMATION FOR SEQ ID NO:9:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
        / note="Ac represents an acetylated amino terminus"

( i x ) FEATURE:
        ( A ) NAME/KEY: Binding-site
        ( B ) LOCATION: 3
        ( D ) OTHER INFORMATION: /note="Metal ligand coordinating contact site"

( i x ) FEATURE:
        ( A ) NAME/KEY: Binding-site
        ( B ) LOCATION: 7
        ( D ) OTHER INFORMATION: /note="Metal ligand coordinating contact site"

( i x ) FEATURE:
        ( A ) NAME/KEY: Modified-site
        ( B ) LOCATION: 19
        ( D ) OTHER INFORMATION: /label=CONH2
        / note="CONH2 represents an amidated carboxyl terminus"

( x i ) SEQUENCE DESCRIPTION: SEQ ID NO:9:

Ala Ala Cys Ala Leu Glu His Gln Ala Lys Ala Leu Lys Glu Ala Ala
1               5                   10                  15

Gln Lys Ala ( 2 ) INFORMATION FOR SEQ ID NO:10:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
        / note="Ac represents an acetylated amino terminus"

( i x ) FEATURE:
        ( A ) NAME/KEY: Binding-site
        ( B ) LOCATION: 3
        ( D ) OTHER INFORMATION: /note="Metal ligand coordinating contact site"

( i x ) FEATURE:
        ( A ) NAME/KEY: Binding-site
        ( B ) LOCATION: 7
        ( D ) OTHER INFORMATION: /note="Metal ligand coordinating contact site"

( i x ) FEATURE:
        ( A ) NAME/KEY: Modified-site
        ( B ) LOCATION: 19
        ( D ) OTHER INFORMATION: /label=CONH2
        / note="CONH2 represents an amidated carboxyl terminus"

( x i ) SEQUENCE DESCRIPTION: SEQ ID NO:10:

Ala Ala His Ala Leu Glu Cys Gln Ala Lys Ala Leu Lys Glu Ala Ala
1               5                   10                  15

Gln Lys Ala ( 2 ) INFORMATION FOR SEQ ID NO:11:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
        / note="Ac represents an acetylated amino terminus"

( i x ) FEATURE:
        ( A ) NAME/KEY: Modified-site
        ( B ) LOCATION: 3
        ( D ) OTHER INFORMATION: /label=Xaa
        / note="Xaa represents a non-natural bipyridyl amino acid with the chemical formula - NH2CH[R]-CO2H, where R =[CH2]n-NHC[O]-3-[N,N'-bipyridine], and n=3."

( i x ) FEATURE:
        ( A ) NAME/KEY: Modified-site
        ( B ) LOCATION: 7
        ( D ) OTHER INFORMATION: /label=Xaa
        / note="Xaa represents a non-natural bipyridyl amino acid with the chemical formula - NH2CH[R]-CO2H, where R =[CH2]n-NHC[O]-3-[N,N'-bipyridine], and n=3"

( i x ) FEATURE:
    ( A ) NAME/KEY: Binding-site
    ( B ) LOCATION: 3
    ( D ) OTHER INFORMATION: /note="Metal ligand coordinating contact site"

( i x ) FEATURE:
    ( A ) NAME/KEY: Binding-site
    ( B ) LOCATION: 7
    ( D ) OTHER INFORMATION: /note="Metal ligand coordinating contact site"

( i x ) FEATURE:
    ( A ) NAME/KEY: Modified-site
    ( B ) LOCATION: 19
    ( D ) OTHER INFORMATION: /label=CONH2
    / note="CONH2 represents an amidated carboxyl terminus"

( x i ) SEQUENCE DESCRIPTION: SEQ ID NO:11:

Ala Ala Xaa Ala Leu Glu Xaa Gln Ala Lys Ala Leu Lys Glu Ala Ala
1               5                   10                  15

Gln Lys Ala ( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ac
    / note="Ac represents an acetylated amino terminus"

( i x ) FEATURE:
        ( A ) NAME/KEY: Modified-site
        ( B ) LOCATION: 3
        ( D ) OTHER INFORMATION: /label=Xaa
    / note="Xaa represents an aminodiacetic amino acid with the chemical formula - NH2CH[R]-CO2H, where R =[CH2]nN[CH2CO2H]2, and n=3"

( i x ) FEATURE:
        ( A ) NAME/KEY: Modified-site
        ( B ) LOCATION: 7
        ( D ) OTHER INFORMATION: /label=Xaa
    / note="Xaa represents an aminodiacetic amino acid with the chemical formula - NH2CH[R]-CO2H, where R =[CH2]nN[CH2CO2H]2, and n=3"

( i x ) FEATURE:
        ( A ) NAME/KEY: Binding-site
        ( B ) LOCATION: 3
        ( D ) OTHER INFORMATION: /note="Metal ligand coordinating contact site"

( i x ) FEATURE:
        ( A ) NAME/KEY: Binding-site
        ( B ) LOCATION: 7
        ( D ) OTHER INFORMATION: /note="Metal ligand coordinating contact site"

( i x ) FEATURE:
        ( A ) NAME/KEY: Modified-site
        ( B ) LOCATION: 19
        ( D ) OTHER INFORMATION: /label=CONH2
    / note="CONH2 represents an amidated carboxyl terminus"

( x i ) SEQUENCE DESCRIPTION: SEQ ID NO:12:

Ala Ala Xaa Ala Leu Glu Xaa Gln Ala Lys Ala Leu Lys Glu Ala Ala
1           5                        10                      15

Gln Lys Ala

METALLOPEPTIDES HAVING STABILIZED SECONDARY STRUCTURES

DESCRIPTION

Technical Field

The present invention relates to metallopeptides having stabilized secondary structures, and to methods for producing structure-stabilized metallopeptides.

Background

Metalloproteins are a class of proteins having a metal ion complexed with the protein molecule at the protein's metal-binding site. The metal ion provides features to a metalloprotein such as facilitating electron transfer, oxidation, or reduction reactions and the like.

The stereochemistry of metal ion complex structure in association with protein has been extensively characterized. Studies of known metalloproteins have resulted in characterization of many metal ions that participate in metal protein complexes, which helps to identify the nature of the metal-protein complex. Three dimensional crystal structures of metalloproteins are available and provide further insight into the nature and structure of the metalloprotein complexes. See, for example, the structures identified for naturally occurring metalloproteins, namely thermolysin, superoxide dismutase and carbonic anhydrase. Holmes et al., *J. Mol. Biol.*, 160:623-639 (1982); Tainer et al., *Nature*, 306:284-287 (1983); and Eriksson et al., *Proteins: Struct. Funct. Gen.*, 4:274-282 (1988).

Interest in producing proteins with increased structural stability has motivated investigators to introduce a variety of conformational constraints in the polypeptide structure of a protein. See, for example, Kemp et al., *Tetrahedron Lett.*, 29:4931 (1988); Arrhenius et al., *Protein Structure and Design II: UCLA Symp. Mol. Cell. Biol. New. Ser.*, 69:453 (1987); Arrhenius et al., *Vaccines*, p. 17 (1989); Felix et al., *Int. J. Pept. Prot. Res.*, 32:441 (1988). Conformational constraint approaches have been motivated because formation of secondary structure in disordered polypeptides requires a first nucleation event, with the energetically unfavorable formation of the first turn of the secondary structure being rate limiting. See for example, Zim et al., *J. Chem. Phys.*, 31:526 (1959); Sueki et al., *Macromolecules*, 17:1948 (1984); Vasquez et al., *Biopolymers*, 26:351 (1987); Schwartz et al., *Angew. Chem. Int. Ed. Engl.*, 11:568 (1972); and Gruenewald et al., *Biophys. Chem.*, 9:137 (1979). Synthesis of polypeptides incorporating conformational constraints require considerable synthetic effort and have been difficult to apply to larger polypeptides and proteins.

Although stabilization of secondary structure has been reported to be facilitated by metal ions in association with polypeptides, structural data indicates that those stabilized metallocomplexes typically involve three or more amino acid residue side chains as donors for ligands to the metallocomplex.

BRIEF SUMMARY OF THE INVENTION

It has now been discovered that polypeptide secondary structures can be stabilized through the incorporation of two amino acid residues in the polypeptide chain that provide side chains to form ligands with a metal ion. Thus incorporation of selected amino acid residues into an amino acid residue sequence that defines a secondary structure provides metal ligand contact sites necessary to form a metal binding site on the polypeptide, thereby producing a metallopeptide having stabilized secondary structure.

BRIEF DESCRIPTION OF DRAWINGS

In the drawings, forming a portion of this disclosure.

In panel 3B, the CD spectrum of peptide 1 ($2.2 \times 10^{-6}$M) in water at pH 6.65 and 4° C. (dotted curve), and in $7.3 \times 10^{-4}$M $CdCl_2$ solution, pH 6.7, at 4° C. (solid curve) is graphed. The presence of a metal ion at 4° C. results in increased alpha-helix stabilization compared to a solution without metal ions.

In panel 3C, the CD spectrum of peptide 2 ($1.8 \times 10^{-6}$M in 5 mM sodium borate, pH 6.1 at 21° C.) in the presence of the following concentrations of $CuSO_4$ is shown (solid curves): 0, $3.3 \times 10^{-5}$, and $6.6 \times 10^{-5}$M. The curves decrease at 220 nm as the metal cation concentration increases. The dashed curve shows the CD spectrum of peptide 2 ($1.8 \times 10^{-6}$M) in 5 mM sodium borate, $7.4 \times 10^{-5}$M $CuSO_4$, pH 6.4 at 0° C.

The CD spectra of metal ion containing peptide solutions decreases as the concentration of the metal ion increases reflecting increased alpha helix formation. This property is enhanced in solutions at 0° C.

Figure 4:
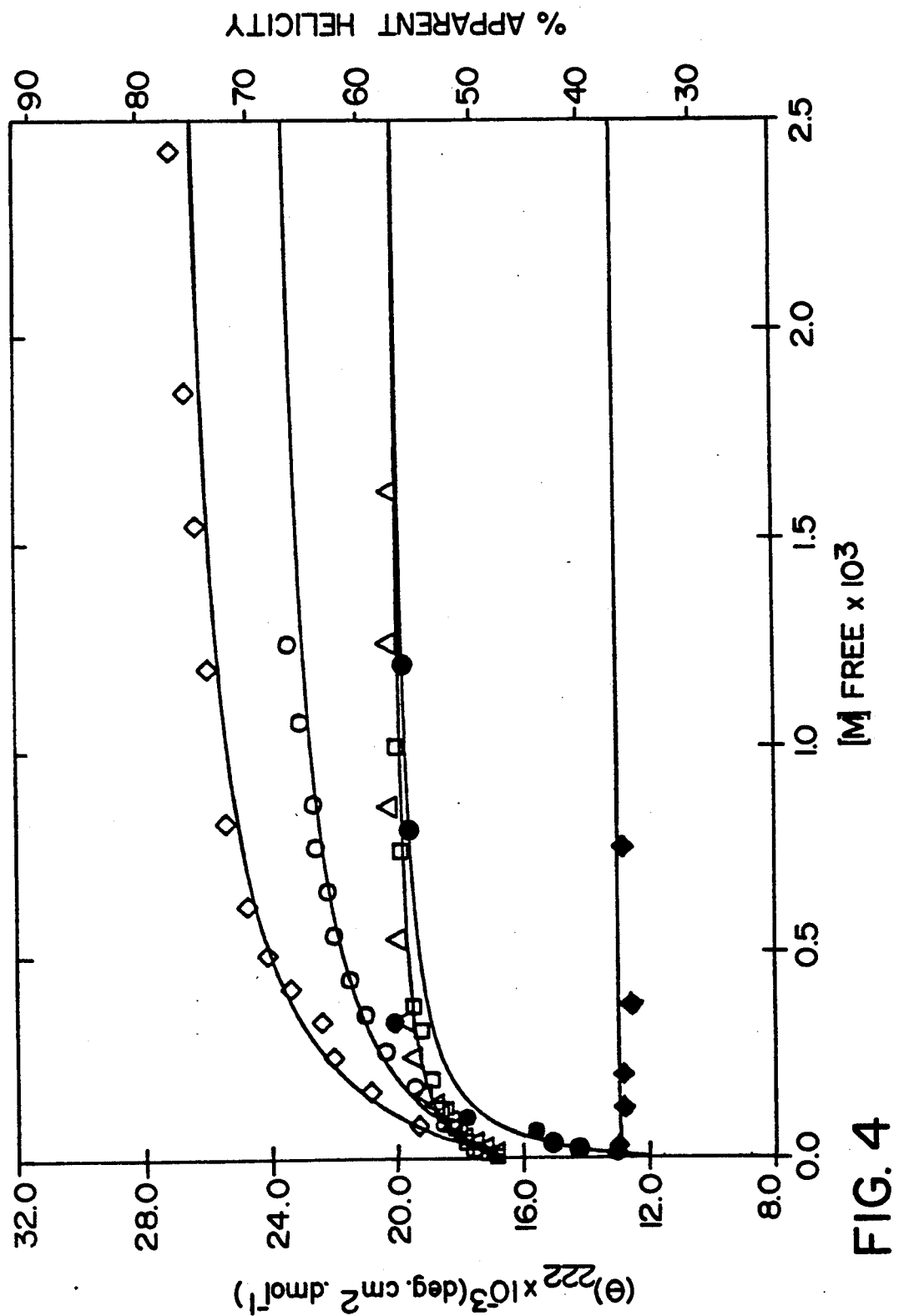

FIG. 4 illustrates the dependence of mean residue molar ellipticity at 222 nm of peptides 1 and 2 on the concentration of free metal ions when measured as described in Example 3A(2). Peptide 1 is at $5.9 \times 10^{-6}$M in 10 mM sodium borate, 0.5 mM mercaptoethanol, 21° C. and was combined with the following metal cations at various concentrations under the indicated conditions and assays (closed circles)$CdCl_2$,pH 8.0, $K_d = 5.6 \times 10^{-5}$M; (closed diamonds)$ZnCl_2$ pH 8.0. Peptide 2 at ($6.1 \times 10^{-5}$M in 5 mM sodium borate, 21°

C. was similarly combined and assays: open triangles)$ZnCl_2$, pH 7.5 $K_d=7.5\times10^{-5}$M; (open squares) $CuCl_2$, pH 5.3, $K_d=6.6\times10^{-5}$M; (open circles) $CdCl_2$, pH 7.5 $K_d=2.2\times10^{-4}$M; (open diamonds) $NiCl_2$, pH 6.3, $K_d=2.1\times10^{-4}$M. The curves were fit to the data by using nonlinear least-squares method. The results indicate that metal ions have different affinities depending on the metal binding site in the synthetic peptide. $NiCl_2$ exhibits the highest affinity followed by $CdCl_2$ for peptide 2. $CdCl_2$ exhibits a greater affinity for peptide 1 than $ZnCl_2$.

Figure 5:
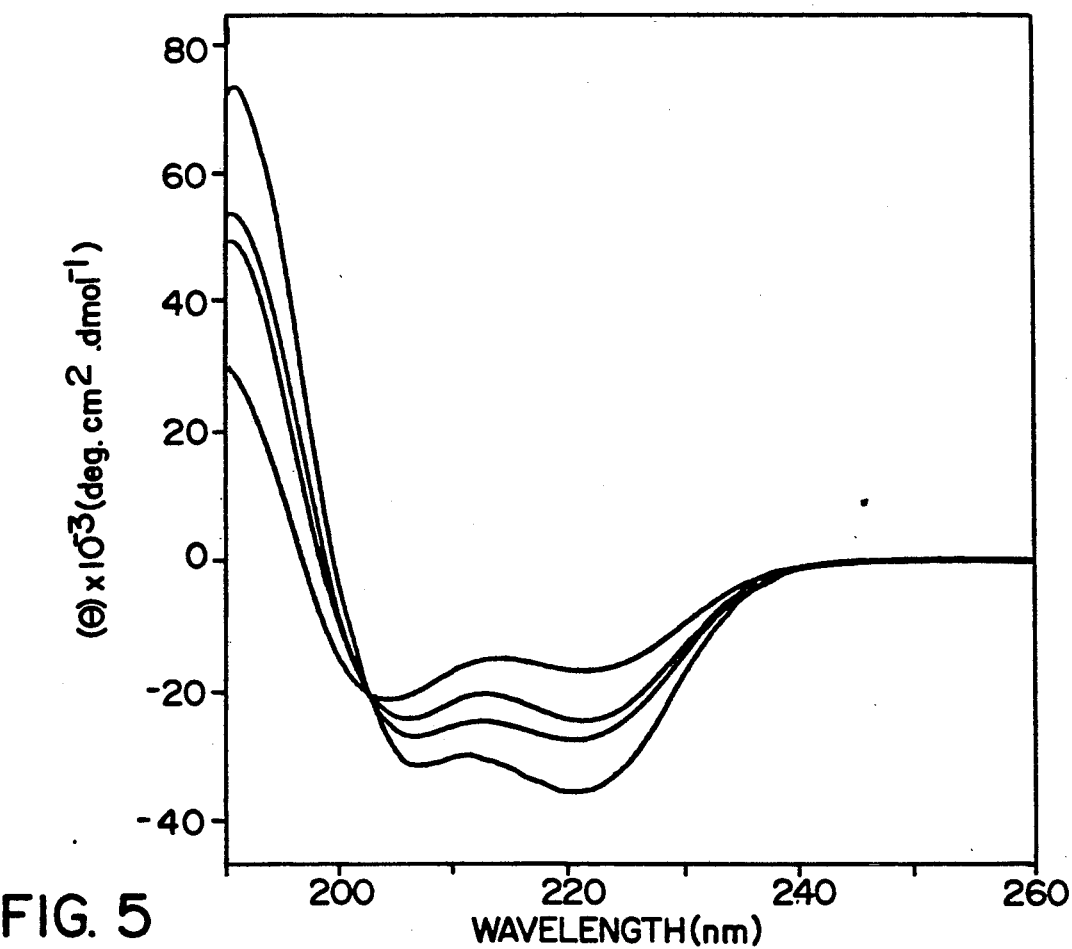

FIG. 5 illustrate s the CD spectra of ruthenium (III) complexed peptides 2 and 3 when measured as described in Example 3A(4). From top curve (arrow) to the bottom curve, (a) cis-Ru(NH$_3$)$_4$-peptide 3, $6\times10^{-6}$M in water, pH 6.0, at 20° C., and (b) at 0° C., (c) cis-Ru(NH$_3$)$_4$-peptide 2, $5.0\times10^{-6}$M in water, pH 6.1, at 20° C., and (d) at 0° C. Ruthenium(III) complexed peptides exhibit increased alpha-helicity in water compared to free peptides which are either partially helical or in random coil structures.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature as described in J. Biol. Chem., 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| J | Xaa | non-natural amino acid |

It should be noted that all amino acid residue sequences are represented herein by formulae whose left and right orientation is in the conventional direction of amino-terminus to carboxy-terminus. In addition, the phrase "amino acid residue" is broadly defined to include naturally occurring and non-naturally occurring (unnatural) amino acid structures. Furthermore, it should be noted that a dash at the beginning or end of an amino acid residue sequence indicates a peptide bond to a further sequence of one or more amino acid residues or to a amino-terminal group such as NH$_2$ or acetyl (Ac) or to a carboxy-terminal group such as COOH or primary amide (CONH$_2$).

Polypeptide or Peptide: refers to a linear series of amino acid residues connected to one another by peptide bonds between the alpha-amino group and carboxy group of contiguous amino acid residues.

Protein: refers to a linear series of greater than 50 amino acid residues connected one to the other as in a polypeptide.

Synthetic polypeptide: refers to a chemically produced chain of amino acid residues linked together by peptide bonds that is free of naturally occurring proteins and fragments thereof.

"Heat stabilized" when used in association with a peptide or protein refers to an amino acid sequence having the modifications described herein that produce a metal binding site such that the resulting metallopeptide exhibits greater structural stability at a given temperature than the corresponding amino acid sequence lacking the heat stabilizing modifications.

B. Metallopeptides and Metallopeptide Compositions

A metallopeptide of this invention comprises a polypeptide having an amino acid residue sequence that includes a sequence of amino acid residues capable of forming a secondary structure rather than a random coil structure in aqueous solutions.

Models for secondary structures of proteins and polypeptides are generally well understood and these structures can include alpha helices and beta strands, including a beta turn region. Insofar as polypeptide secondary structures are three dimensional, they can be amphipathic. An alpha helix or beta strand is amphipathic when it can be divided into separate faces, namely a hydrophobic (non polar) region and hydrophilic (polar), or solvent accessible region. For a comprehensive review of protein structures, see "Prediction of Protein Structure and the Principles of Protein Conformation", Ed. G. D. Fasman, Plenum Press, N.Y. (1989). The references cited therein are hereby incorporated by reference.

The characterization of alpha helical and beta strand secondary structures in proteins and polypeptides can be accomplished by a variety of optical measurement techniques including circular dichroism or Raman spectroscopy, and by x-ray crystallographic means. In addition, predictive models of secondary structure, including identification of hydrophilic regions in a secondary structure, can be prepared by the use of computer-based modeling programs when applied to known primary amino acid residue sequences. Exemplary predictive conformation programs and models are described in "Prediction of Protein Structure and the Principles of Protein Conformation" ed. G. D. Fasman, Plenum Press, N.Y., (1989), and particularly in Appendices 1 through 5 of the above book at pages 303–316.

A metallopeptide of this invention is further characterized as a polypeptide complexed with (bound to) a metal cation through ligands provided by a pair of coordinating amino acid residues in the polypeptide. The pair of coordinating amino acid residues provide ligand contacts to the metal ion in a geometry that coordinates the complexation of the metal cation. Thus, the pair of coordinating amino acid residues form a metal binding site on the polypeptide by providing metal-ligand coordinating contacts for complexing the metal cation. Furthermore, the polypeptide is bonded to the metal cation such that the metallopeptide has a secondary structure that is stabilized by the bonded metal cation.

The structure and stereochemistry of metal-polypeptide interactions in metalloproteins is generally well understood. See, for example, Freeman et al., *Adv. Protein Chem.*, 22:257–424 (1967); Kannan et al., *Annals. N.Y. Acad. Sci.*, 429:49 (1984); and Tainer et al., *J. Mol. Biol.*, 160:181–217 (1982). Additional metalloprotein structures are described in three dimensions by the crystal structure information in the Brookhaven Data Bank, and by the glossary of metalloproteins and individual references to each of the metalloproteins found in Appendix 1 of "Prediction of Protein Structure and the principles of Protein Conformation", ed. Fasman, at page 91–94, Plenum Press, N.Y. (1989). However, the metalloproteins previously characterized involve at least three amino acid residues that provide metal-ligand coordinating contacts to complex with a metal ion.

In a metallopeptide of this invention, each of said pair of coordinating amino acid residues provides at least one metal-ligand coordinated contact. Thus, a metal binding site in a metallopeptide of this invention is formed by two, but not three, coordinating amino acid residues.

In one embodiment, the coordinating amino acid residue is of a type that provides more than one metal-ligand coordinated contact, i.e., is bidentate, tridentate, quadentate, and the like, as discussed herein. Thus, a coordinating amino acid residue provides at least one, but not more than four metal-ligand coordinated contacts.

A metal binding site is engineered into a polypeptide by the teachings of this invention for the purpose of stabilizing a secondary structure of the polypeptide by the formation of a metallopeptide complex. The complex is present in a composition that typically includes aqueous solvent, and the metal binding site is positioned on the polypeptide so as to be on an aqueous solvent accessible surface, e.g., on a hydrophilic surface region of the polypeptide's secondary structure. Thus, a metal binding site, and the pair of coordinating amino acid residues, are located in a surface region (a solvent exposed hydrophilic surface) of the polypeptide's secondary structure in order to allow access of the metal binding site to dissolved metal cations in solution.

Compositions containing a metallopeptide of the present invention are also contemplated.

In a broad embodiment, therefore, the present invention contemplates a metallopeptide composition having a stabilized secondary structure comprising a polypeptide having an amino acid residue sequence, a portion of which sequence forms a secondary structure that includes a hydrophilic region, and a pair of coordinating amino acid residues that defines a metal binding site located in the hydrophilic region, i.e., the coordinating amino acid residues are solvent accessible, and further comprises a metal cation complexed through metal-ligand coordinating contacts to the metal binding site such that each coordinating amino acid residue provides at least one metal-ligand coordinating contact.

In preferred embodiments, the polypeptide of a metallopeptide composition comprises an amino acid residue sequence capable of forming an alpha helix or beta strand and beta turn secondary structure with a hydrophilic surface when present in an aqueous solution.

Where the secondary structure is an alpha helix, the preferred positions of the two coordinating amino acid residue are at the relative positions of i and i+4 on the polypeptide such that the side groups of the residues extend away from the helix and hydrophilic surface and into the adjacent aqueous solvent of the composition. Stated differently, the coordinating amino acid residues of the metallopeptide are separated by three spacer residues according to the formula —Z—U—U—U—B—, where Z and B represent the same or different coordinating amino acid residues and U represents the same or different amino acid residue, preferably a natural residue.

Where the secondary structure is a beta strand having a beta turn, the preferred positions of the two coordinating amino acid residues are at the relative positions of i and i+3 or at the relative positions of i−1 and i+5 on the polypeptide such that the side groups of the residues extend away from the plane defined by the beta strand and beta turn and extend into the adjacent aqueous solvent of the polypeptide. Thus the coordinating amino acid residues of the metallopeptide are separated by two or five spacer residues according to the formula —Z—U—U—B— or —Z—U—U—U—U—U—B—, respectively, where Z, B, and U are defined as above. In a beta turn structure that includes both a beta strand and a beta turn, conventional nomenclature identifies the residue located in a beta strand at a position one residue prior to the beginning of the turn as residue i. Thus the position i−1 is located two residue positions prior to the beginning of a beta turn.

In practicing the invention, i.e., of preparing and using metallopeptide having stabilized secondary structures, it is important to appreciate the mechanism of stabilization in order to determine the possible locations of an engineered metal binding site. Secondary structures, such as alpha helices and beta sheets that contain beta strands and beta turns are kinetically unfavorable until sufficient interaction occurs between residues of the polypeptide as to overcome the random coil structure. These principles are particularly applicable to smaller polypeptides where the disordered structure is less likely to fold is the particular conformation so as to produce a stabilizing interaction. The nucleating event in the formation of an ordered structure is the stabilization and formation of a first turn, which is the least favorable and therefore rate limiting step. Once the first turn of an alpha helix is stabilized, the translocation of stabilization down a region of a polypeptide having potential to form a helix is catalytic. Thus the localized stabilization of a pair of residues into the first turn of a helix by metal-polypeptide complex formation will promote stabilization along the length of the helix. This nucleation event, therefore, can lead to the stabilization of a first helix, which in turn can provide support to stabilize more distant secondary structures such as alpha helices or beta strands. Just as the nucleation event will stabilize an alpha helix, so does such an event stabilize an entire beta sheet by nucleating at a beta turn and translocating down any beta strands beginning at the beta turn.

Thus, in the context of stabilization by nucleation, a metal binding site can stabilize a larger polypeptide secondary structure, and contribute to stabilization of a polypeptide's tertiary structure.

The translocation of stabilization is an important feature of the present invention. Where the polypeptide to be stabilized is a biologically active molecule, it contains a site for molecular interaction that is required for biological function that will not be sterically hindered by a metal ion complexing with a metal binding site. In these cases it is advantageous to position the stabilizing metal binding site away from the polypeptide's biologically active site. Translocatable stabilization makes it possible to engineer known biologically active polypeptides without disrupting biological function by locating the metal binding site away from the biologically active region.

An amino acid residue that is present in a metallopeptide and provides a metal-ligand coordinated contact with a metal ion is referred to herein as a coordinating amino acid residue. Amino acid residues suitable for use as a coordinating amino acid residue in a metallopeptide of this invention are the natural amino acid residues known in the metalloprotein arts to provide a ligand for metal cations in metalloproteins, and include histidine, cysteine, methionine, and the like residues.

In preferred embodiments pairs of coordinating amino acid residues can be histidine and histidine, histidine and cysteine or histidine and methionine. Particularly preferred is the pair where each coordinating amino acid residue is histidine.

In addition to the natural amino acids that can be practiced with the present invention as described above, non-natural amino acids may also be employed, e.g., amino acid analogs. A clear advantage of using non-natural amino acids is that much more flexibility can thereby be built into the selection of pairs of amino acids which serve to connect the polypeptide backbone to an appropriate metal center. The non-natural amino acids may also be used in conjunction with natural amino acids appropriately spaced apart along the polypeptide chain so that the desired alpha helixes or beta sheets may be stabilized. The natural amino acids suitable for use in the latter application are identical to those described above.

The process of selecting suitable non-natural amino acids for use in the present invention will parallel the selection of natural amino acids in the invention. For example, preferred embodiments of the natural amino acids identified above include nitrogen or sulfur atoms which bind directly to the metal center, e.g., histidine and cysteine. Similarly, preferred non-natural amino acids will also incorporate a nitrogen and/or a sulfur center for binding to the bridging metal ion.

A further consideration in the selection of suitable non-natural amino acids for use in the present invention is the "chelate effect". The "chelate effect" is well known in the art of coordination chemistry and explains why ligands having more than one binding center (metal-ligand coordination contact) show a greater propensity for binding a metal ion than ligands having only one binding center. The nature of the bonding between metal and ligand is usually characterized as ionic but it may also be of the covalent type. The chelate effect is a thermodynamic phenomenon in which the stability of a metal-ligand complex is enhanced due to an increase in entropy upon dissociation of solvent molecules from the metal's coordination sphere upon chelation. Thus, ligands (coordinating amino acid residues) will bind strongly and preferentially when they can chelate the metal cation.

In identifying the pair of coordinating amino acid residues and metal ion most suited for stabilizing a particular alpha helix or beta sheet secondary structure, the primary criterion will be that the ligands bind strongly with the selected metal atom under the relevant reaction conditions. Other variables, such as the length of side chains connecting the binding terminal groups of non-natural amino acids with the polypeptide backbone, can be determined after the appropriate ligand has been identified. This is because the length of the side chain will depend upon the type of ligand selected.

Generally, the identification of preferred ligands for binding metal can be made by either first determining the ligand group desired to be attached to the polypeptide backbone, then identifying metal ion centers that bind strongly to that ligand, or the desired metal ion may be first identified with preferred ligands identified subsequently. Thus, a preferred ligand binding pair may be identified and then metal candidates can be screened for their effectiveness in binding the ligand groups. Alternatively, ligand groups can be screened following identification of a preferred metal binding ion. Such methods of screening are well known to those skilled in the art.

Several guiding principles allow narrowing the selection of efficacious ligand-metal binding pairs. Most prominently, preferred metal-ligand binding pairs may be identified phenomenologically. Therefore, ligands that bind preferentially to the metal in the presence of water will be initially preferred candidates in the present invention. Such ligands can be identified by noting the relative binding efficiencies of metals and metal complexes for such ligands or their analogs in the presence of water. An example of this principle is illustrated in the case of $Ru(NH_3)_5 \cdot (H_2O)$ (ruthenium aquapentamine cation), which is well known to fix nitrogen in aqueous solution. See, H. Taube, et al., *JACS* 89:5706 (1967). Thus this complex is identified as a likely candidate for binding N-lewis base-containing ligands. Similarly, [cis-ruthenium tetraamine]$^{+2}$ is expected to be a good candidate for binding nitrogen containing ligand bases. Additionally, ligands having the capacity to act as good chelaters will be preferred candidates for coordinating to a metal cation.

Another useful consideration identifying candidates for screening effective metal-ligand binding pairs is afforded by the Hard-Soft-Acid-Base (HSAB) thereby proposed by Pearson. See also J. Huheey, *Inorganic Chemistry*, Harper & Row (1972), p. 225-35. According to the HSAB theory "hard acids" have a preferred tendency to bind to "hard bases" while "soft acids" have a tendency to bind to "soft bases". Thus metals in high oxidation states have a tendency based on their charge/radius ratios to bind to anions having high charge/radius ratios or to neutral ligands having relatively localized electron densities, e.g., hydrated metal ions and electropositive metals. On the other hand, soft acids, such as metals in their low or zero valance states have a tendency to bind to soft ligands that can accept electron density from the metal, e.g., metal carbonyl and metal-olefin compounds. The metal orbital constraints on binding presented by a given metal ion are a secondary consideration in determining efficient binding and generally will not present an obstacle to identifying efficient binding pairs. Instead, considerations of charge/radius ratio and polarizability of the ligand will predominate.

Polypeptides prepared according to the present invention will have coordinating amino acids substituted at appropriate spacings along the polypeptide backbone. The side chains of these amino acids and amino acid analogs will have a spacer group that serves to link the polypeptide backbone to the binding moiety located at the terminal end of the side chain. Suitable spacing groups include methylene chains, phenyl groups, and combinations thereof. Also preferred linking groups will include amido groups which serve to connect the terminal binding group to the side chain. Many other spacing groups will be apparent to the skilled practitioner.

Factors considered in the identification of suitable spacer groups will include the thermal stability of the spacer group and the ability of the spacer group to avoid interfering with forming alpha helices or beta sheets in the folded protein chain. Another important factor in identifying a suitable spacer group will be the facility of linking a separately prepared ligand to an amino acid. Preferably, the amino acid will contain the side chain as well as a reaction site that will readily react with the separately prepared ligand (ligand precursor). Exemplary of such reaction schemes is the condensation of an acid group on the side chain with a reactive amino group on the ligand precursor, as well as condensation of a side chain amino functionality with a carboxyl group on the precursor.

A preferred nonnatural amino acid has diacetato amino (DAA) terminus on its side chain. The DAA group will preferably be incorporated into a resin bound peptide incorporating two ornithines in the amino acid sequence corresponding to the location of the coordinating amino acids. Thus, ornithines will be preferentially blocked with tBoc in an FMOC blocked polypeptide. The Boc groups are removed with TFA and then reacted with excess benzyl bromo acetate in diisopropyl ethyl amine. The N atom of the amino acid is then coupled to acetate groups. Finally, the FMOC group is removed to give a terminal amino group which can be acetylated if desired.

A second approach to coupling binding moieties to amino acid side chains involves forming an amido linkage. Thus, 6-chloro nicotinic ester and trimethyl tin pyridine in the presence of dichloro-bis (triphenylphosphino) palladium catalyst. The product is saponified, then protonated to give 4-carboxyl bipyridine, which is then combined with deproteinated ornithine and dicyclohexyl carbodiimide to form the amido linkage.

Another method of coupling a binding moiety, e.g., N-N chelating group, to an amino acid, involves making the BOC derivative of benzyl-aspartate. The product is coupled to 4-amino bipyridine in DMF in the presence of carbodiimide. The amide carbonyl group is reduced with hydrogen over Pd and charcoal in ethanol. The resulting bidentate amino acid is incorporated into the peptide using standard tBOC chemistry.

Preferred terminal groups that coordinate to the bridging metal ion will be those groups that effectively compete with water for coordination sites on the metal. As described above, the preferred ligand will depend upon the selected metal, or vice versa, the selected metal will depend upon the preferred ligand. For example, when a preferred ligand contains a nitrogen lone pair (as when Ru(II) or Ru(III) are used as the stabilizing metal ion), any N-containing compound having a Lewis basicity attributable to the nitrogen lone pair can be used, e.g. pyridine linked to an amino acid. Similarly, whenever the nitrogen center is negatively charged, e.g., with N-pyrrole and porphyrin-like compounds, strong binding pairs can be expected with the metal ion. Additionally, the chelate effect associated with a given ligand will assist in identifying still further preferred binding groups. Preferably, two or three coordination sites on the metal will be occupied by such a chelating group.

Exemplary nitrogen chelating ligands which are preferred embodiments of the present invention include phenanthroline and bipyridine ligands. Such ligands will occupy two coordination sites on a preferred metal center. The phenanthroline and bipyridine ligands can be linked to the polypeptide backbone conveniently by condensation between the respective N-ligand and a suitable functional group extending from an amino acid backbone unit. For example, aspartic acid or glutamic acid can be linked via the side chain carboxyl group to phenanthroline or bipyridine moieties upon condensation of the amino acid with an amino derivative of the corresponding N-ligand. This reaction is illustrated in the following equation:

$$\text{Asp} + \text{NH}_2\text{-bipyridine} \rightarrow \text{Asp-NH-bipyridine} + \text{H}_2\text{O}$$

Analogously, whenever the preferred binding ligand contains 1-3 sulfur (neutral or anionic) atoms, the ligand may be linked via an alkylidene side chain and condensation linkage, and the like. Also combinations of nitrogen-containing ligands and sulfur-containing ligands can be employed to coordinate the metal atom.

Other examples of nitrogen derivatives which may be identified as preferred binding ligands in the present invention include such monodentate ligands as pyridine and pyrazine linked via a spacing group to the backbone chain of the polypeptide. Also such chelating ligands as 1,2-diaminoethane and bispyridylmethane may be employed. A still further preferred embodiment will employ porphyrin-like chelating ligands that upon deprotonation bind strongly to the metal center in bidentate fashion.

Alternative preferred ligands include tridentate ligands such as diacetato amine and tetra dentate ligands such as triethylene tetramine. Other mono-, bi-, tri- and tetra-(quad) dentate ligands are presented in Table 1 and still others will be apparent to the skilled practitioner. Accordingly, the ligands selected will typically form 5 and 6 member rings with the metal ions.

TABLE 1[a]

| Side Chain[b] | Parent Compound |
| --- | --- |
| 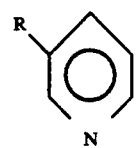 | pyridine |
|  | aniline |

TABLE 1(a)-continued

| Side Chain(b) | Parent Compound |
|---|---|
| (structure with R, NH, N) | 3-azapyrrole |
| (structure with R, N, N) | pyrimidine |
| (structure with R, H₂N, NH₂) | 1,2-diaminoethane |
| (structure with R, two pyridine rings, N, N) | 2,2'-bipyridine |
| (structure with R, bipyridine with methylene) | 6-6' methylene bipyridine |
| (structure with R, three fused rings, N, N) | 1,10-phenanthroline |
| (structure with R, pyrrole rings, H—N) | hemiporphyrin |
| (structure with R, H₂N—NH—NH—NH₂) | triethylenetetramine |
| (structure with R, pyridine, CO₂H, N) | 2-carboxypyridine |
| R—N(CO₂H)(CO₂H) | amino-diacetic acid |
| R—S—H | hydrogen sulfide |
| (structure with R, benzene ring, SH) | mercaptobenzene |
| (structure with R, HS, SH) | 1,2-dimercaptoethane |
| (structure with R, two thiophene rings, S, S) | 2,2'-bithiophene |
| (structure with R, thiophene, CO₂H, S) | 2-carboxythiophene |

(a) $NH_2-CH-CO_2H$
        |
     side chain (b) R = spacer group, e.g., $(CH_2)_n$; —C(O)—NH—; —NH—C(O)—

Preferred embodiments include coordinating amino acid residues according to the formula: $HO_2C-CH(-R)-NH_2$, where $R=(CH_2)_n-N(CH_2CO_2H)_2$ and n=1,2,3 or 4. Particularly preferred is the non-natural amino acid residue where n=3. A polypeptide including this preferred coordinating amino acid residue is shown in Table 2 and is designated peptide 12.

Additional preferred embodiments include coordinating amino acid residues according to the formula: $HO_2C-CH(R)-NH_2$, where $R=(CH_2)_n-NH-C(O)-4-[2,2'-bipyridyl]$, and n=1,2 or 3. Particularly preferred is the non-natural amino acid residue where n=3. A polypeptide including this preferred coordinating amino acid residue is shown in Table 2 and is designated peptide 11.

More preferred embodiments include coordinating amino acid residues according to the formula: $HO_2C-CH(R)-NH_2$, where $R=(CH_2)_n-NH-C(O)-5-[1,10-phenanthroline]$ and n=1,2 or 3.

Alternatively, the selected binding ligands may each incorporate a combination of different types of binding moieties that together coordinate the identified metal binding center. For example, a diacetatoamino group may be appended to the terminal end of the side chain to generate a non-natural amino acid that coordinates strongly to the metal center. Similarly, combined amino-sulfide ligands, aminophosphate, amino sulfonato, amino-carboxylate, and amino-phosphino ligands may be used to chelate the bridging metal ion in a preferred mode to enhance the stability of the polypeptide or protein secondary structure.

Once the non-natural amino acids have been incorporated into the polypeptide chain the resulting modified polypeptide may be reacted with the preferred metal cation by simply admixing the polypeptide compound in aqueous solution with a suitable salt of the identified metal ion. Polypeptides will react with the metal ion, via their ligand-attached side chains, expelling water molecules from the coordination sphere of the metal ion. The metal ion will react with two ligands in bridging fashion. Once the bridging metal-containing complexes form it will operate in an "exchange-inert" manner to maintain the integrity of the ligand-metal binding structure, thereby stabilizing the secondary structure of the polypeptide or protein under the reaction conditions. Preferred ligands will be exchange-inert with the metal's coordination sphere, i.e., once the ligand is coordinated to the metal it will have only a slight tendency to dissociate from the metal.

Polypeptide compositions may also be prepared according to the principles of the present invention in which a selected polypeptide coordinated to a metal ion is prepared for subsequent binding to a target polypeptide or a protein structure. More typically, the polypeptide composition will comprise a target protein having a secondary structure that is desired to be enhanced. The protein will be bound to a preselected metal ion via two naturally occurring amino acids or one naturally occurring amino acid linked to a non-naturally occurring amino acid at the appropriate separation distance or to non-naturally occurring amino acids linked via the metal ion. Such compositions will have enhanced stability in aqueous solution due to the metal-ligand complex structure adopting favored alpha helix or beta sheet conformations in solution.

A metal cation suitable for use as a component of a metallopeptide of this invention can be any metal cation capable of complexing with the polypeptide present in the metallopeptide composition, so long as the complexing occurs with the ligands provided by the two coordinating amino acid residues that define the metal binding site of the metallopeptide.

Typical metal cations include zinc (Zn), cadmium (Cd), copper (Cu), nickel (Ni), ruthenium (Ru), platinum (Pt), palladium (Pd), cobalt (Co), magnesium (Mg), barium (Ba), strontium (Sr), iron (Fe), vanadium (V), chromium (Cr), manganese (Mn), rhodium (Rh), silver (Ag), mercury (Hg), molybdenum (Mo), tungsten (W), calcium (Ca), lead (Pb), cerium (Ce), aluminum (Al) and thorium (Th). The ionic state of metal ions can vary, as is well known, and it is preferred that the oxidation state of a metal cation in a metallopeptide of this invention be one of following where the oxidation state is indicated in parenthesis: Zn(II), Cd(II), Cu(I), Cu(II), Ni(II), Ru(II), Ru(III), Pt(II), Pd(II), Co(II), Co(III), Mg(II), Ba(II), Sr(II), Fe(II), Fe(III), V(III), Cr(II), Cr(III), Mn(II), Rh(III), Ag(I), Hg(II), Mo(III), Mo(IV), Mo(V), Mo(VI), W(III), W(IV), W(V), W(VI), Ca(II), Pb(II), Ce(III), Al(III), and Th(IV).

As is understood by the discoveries of the present invention, no particular metal cation is necessarily required to stabilize a particular polypeptide having a metal binding site comprised of two coordinating amino acid residues. Rather, applying the teachings of this specification, many different metal cations can be selected as suitable for use as a metal cation in a metallopeptide composition. Preferably, the metal cation utilized is that which exhibits the greatest stabilization of the polypeptides secondary structure. The capacity of a particular metal cation to exhibit greater stabilization of a secondary structure when compared to another metal cation is referred to as the preference of a particular metal binding site for complexing with a metal cation. Insofar as the ligands provided by the pair of coordinating amino acid residues form the metal binding site, it is the ligands, the geometry of the ligands in the polypeptide environment, and the chemical properties of the ligands that create a preference for interaction with a particular metal cation.

Metal cation preferences can be identified for any particular metal binding site in a particular polypeptide. See, for example, the results described in Example 3A(2) where the metal cation preferences are identified for the metal binding site formed by peptides 1 and 2. Identification of a preferred metal cation for use in a metallopeptide composition is accomplished by the screening methods for producing a stabilized metallopeptide as described herein.

Stability of the metal-ligand complex in a metallopeptide composition is a desirable feature of the present invention. Stability of the metal-ligand complex is indicated by the conditions under which the ligands of a metal binding site disassociates from the metal cation in the metal-ligand complex. Concomitant with disassociation is a reassociation between the ligands and either a different metal cation or the original metal cation. The process of dissociation and reassociation of a metal-ligand complex is referred to as exchange. In relative terms, stable complexes are more exchange-inert and unstable complexes are more exchange-labile. Exchange inert metal complexes have been previously described and are particularly preferred. For a general discussion of exchange inert metal complexes, see Taube, *Chem.Rev.*, 50:69 (1952); Van Wart, *Meth. Enzymol.*, 158:95 (1988); Barton, *Comm.Inorg.Chem.*, 3:321 (1985); "Metal-Ligand Interactions in Organic Chemistry and Biochemistry", Pullman, et al., Eds., D. Reidel, Boston (1977); Margalit, et al., *J.Amer.Chem. Soc.*, 105:301 (1983); and Friedman, et al. *J. Amer. Chem.Soc.*, 112:4960 (1990).

A metal cation that forms an exchange inert metal complex in a metallopeptide composition, i.e., a stable complex, is preferred over other metal cations because the resulting metallopeptide is more likely to maintain a stabilized secondary structure due to the presence of the complex. The more exchange inert the complex, the higher the melting temperature (Tm) of the metallopeptide secondary structure. Thus, a metallopeptide having a relatively exchange-inert metal complex will be more thermostable, and thereby will impart on the metallopeptide the ability to maintain secondary structures at higher temperatures than a similar metallopeptide with a relatively less exchange-inert metal complex.

Preferred exchange-inert metal complexes are those involving a tetraamonium rutheium(III) complex. Exemplary are complexes having the formula cis-$[Ru(U)_n(L)(L')]^{3+}$ where L and L' are the coordinating ligands provided by a pair of coordinating amino acid residues; where U is either $NH_3$, ethylenediamine(en), triethylenetatraamine(trien), or 2,2'-bipyridine (bipy); and where n is 4 when U is $NH_3$, n is 2 when U is en or bipy, and n is 1 when U is trien.

Ruthenium complexes in the (II) oxidation state are also contemplated as suitable to form exchange inert metal complexes in a metallopeptide composition of this invention. However, Ru(II) forms exchange inert metal complexes that are not as inert as Ru(III) complexes.

In a particularly preferred embodiment, the metal-ligand complex is a tetraamino ruthenium(III) complex in which the ligands are provided by a pair of histidine residues at the relative positions of i and i+4. Exemplary is the peptide 2 Ru(III) complex described in Example 2B.

In another embodiment, termini can be modified in a polypeptide of a metallopeptide composition to further provide stabilization by metal-ligand complex formation. By amidating a native carboxy-termini of a polypeptide, the strong charge dipole at the carboxy-termini is reduced. The reduction in charge facilitates alpha helix stabilization. A charge reduction at the amino-termini, by acetylating the polypeptide amino-termini, can also facilitate helix stabilization. The characteristic of further stabilizing alpha helical secondary structures by removing charge dipoles at the amino and/or carboxy termini also applies to stabilizing beta strand and beta turn structures. Thus, in preferred embodiments, a metallopeptide of this invention also comprises a modified amino or carboxy termini to reduce the charge dipole. Although numerous chemical modifications to the terminal amino acid residues may be used to reduce the charge, preferred modifications are the acetylation of a free amino termini and the amidation of a free carboxy termini.

Insofar as the energetics of stabilization of secondary structures is dependent on the extent of secondary structure, i.e., the length of the alpha helix or beta sheet structure, it is understood that large helical or sheet structures are more energetically favorable than small helical or sheet structures. In this context, the undesirable effect described above of a charged amino or carboxy termini to destabilize a secondary structure is inversely proportional to the size of the particular secondary structure. In practice, modification of termini on very large polypeptides, typically greater than about 30 amino acid residues, and on proteins, does not substantially improve stabilization of secondary structures by metallopeptide complex formation. Thus, the above described modifications of polypeptide termini are preferably limited to smaller peptides having more unstable secondary structures, namely peptides of less than about 30 amino acid residues in length, and preferably of less than about 15 amino acid residues in length.

C. Methods for Preparing a Polypeptide With Stabilized Secondary Structures

A metallopeptide of this invention in one embodiment is prepared to improve the stability in, or to provide stability to, the secondary structures of a polypeptide. The method for preparing a metallopeptide having stabilized secondary structures generally involves the preparation of a preselected polypeptide to include coordinating amino acid residues at preselected regions of the polypeptide to provide a metal binding site. The prepared polypeptide is then complexed with a metal cation to form a metallopeptide having a metal-ligand complex involving coordinated metal-ligand contacts between the complexed metal cation and each of the pair of coordinating amino acid residues.

As described previously, attempts to stabilize secondary structures within polypeptides have proven difficult due to the unique environment of any given polypeptide that defines a secondary structure. Thus, the precise bond lengths involved in, for example, an intra chain covalent linkage to stabilize a secondary structure have been successfully determined only in limited cases where a protein or peptide secondary structure is well characterized.

The present method provides a routine procedure for determining a preferred metal cation to complex with a metal binding site engineered into a polypeptide, thereby allowing the preparation of a metallopeptide having a metal-ligand complex and a resulting stabilized secondary structure.

A key feature of the inventive method is based on the finite yet varied number of metal cations available for a screening step to determine a preferred metal cation for complexing a preselected and engineered metal binding site and thereby rendering more stable the secondary structure of the polypeptide that contains the metal binding site.

Of the metal cations available, a range of metal-coordination bond radii, bond angles, and electron sharing propensities are represented such that at least several of the cations will present the appropriate conditions for metal-ligand complexation. Furthermore, some of the complexing metal cations will form metal-ligand complexes that measurably, and preferably at least, stabilize a secondary structure present in the resulting metallopeptide. Thus, the advantage and benefit to the present invention is the reproducible ease with which to identify a structure-stabilizing metal-ligand complex and thereby form a metallopeptide having a stabilized secondary structure.

By substantial stabilization of a polypeptide's secondary structure is meant that the degree of stabilized secondary structure increases by at least 10 percent, and preferably by at least 50%, when practicing the method for stabilizing a polypeptide's secondary structure.

In practicing the method, a polypeptide or protein having a known amino acid residue sequence is selected for stabilization of secondary structures. The amino acid residue sequence of the protein or polypeptide can be obtained from the published literature, from computerized databases, such as GENBANK, the EMBL protein sequence database, and the like well known sources, or can be determined empirically by conducting protein sequencing or DNA sequencing methods on isolated protein or cloned DNA, respectively, as is also well known.

The amino acid residue sequence of the selected polypeptide (or protein) is then analyzed to identify the presence of regions of amino acid residue sequence capable of forming a secondary structure having a hydrophilic surface (region). These secondary structures include alpha helices and beta strands that include a beta turn, as discussed hereinbefore.

Identifying secondary structures in polypeptides or proteins is now a well developed art. See, for example, the disclosures in "Prediction of Protein Structure and the Principles of Protein Conformation", G. D. Fasman, Ed., Plenum Press (1989), particularly Appendices 1 through 5 at pages 303-316, which disclosure is hereby incorporated by reference.

Alternatively, the secondary structure of a polypeptide or protein may be identified by physical analysis of a specimen of the protein or peptide by, for example, x-ray crystallography and like techniques that provide three dimensional structure data.

A polypeptide, i.e., peptide or protein, is then prepared according to its known amino acid residue sequence that comprises a sequence of amino acid residues capable of forming a secondary structure as defined herein, namely an alpha helix or beta strand and beta turn, except that amino acid residue substitutions are included in the prepared polypeptide to provide a pair of coordinating amino acid residues that form a metal binding site.

The amino acid substitutions to be included to form a pair of coordinating amino acid residues can be any of the amino acid residues defined above for a metallopeptide. Exemplary are the amino acid residues included in the polypeptides produced in Example 1, some of which contain pairs of coordinating amino acid residues comprising natural amino acid residues, and others containing pairs comprising non-natural amino acid residues.

Polypeptides for use in a metallopeptide of this invention, referred to as subject polypeptides, can be prepared by a variety of means, known to those skilled in the polypeptide arts, and the method of polypeptide production is not to be taken as a limitation of the present invention. Rather, any method to produce a polypeptide is suitable so long as it results in a polypeptide having the components described herein.

Polypeptide preparation can be accomplished by using recombinant nucleic acid methodologies well known in the art. For instance, a DNA segment coding for a subject polypeptide can be synthesized by chemical techniques, for example, the phosphotriester method of Mateucci, et al., *J.Am.Chem.Soc.*, 103:3185 (1981). The DNA segment can then be ligated into an expression vector, and a host transformed therewith can be used to produce the polypeptide. See, for example, *Current Protocols In Molecular Biology*, Ausubel, et al., eds., John Wiley & Sons, New York, N.Y.; U.S. Pat. Nos. 4,237,224 and 4,356,270.

Polypeptide synthesis by recombinant nucleic acid methodologies is particularly suited to preparing large polypeptides, namely proteins, particularly those over 100, and most particularly those over 200 residues in length.

A subject polypeptide can also be prepared using the solid-phase synthetic chemistry technique initially described by Merrifield, in *J.Am.Chem.Soc.*, 85:2149–2154 (1963). Synthetic chemistry techniques are preferred for smaller polypeptides, i.e., having less than about 50 residues, for reasons of purity, freedom from undesired side products, ease of production and the like. Other polypeptide synthesis techniques may be found, for example, in M. Bodansky, et al., *Peptide Synthesis*, John Wiley & Sons, 2d Ed. (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104–237, Academic Press, New York, N.Y. (1976). Appropriate protective groups for use in such synthesis will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitable protected is admixed and reacted under conditions suitable for forming the amid linkage with the residue already attached to the solid support. The protecting group of the amino or carboxyl group is then removed from this newly added amino acid residue, and the next amino acid (suitable protected) is then added, and so forth. After all the desired amino acids have been linked in the proper sequence any remaining terminal and side group protecting groups (and solid support) are removed sequentially or concurrently (if desired), to provide the final polypeptide.

Where a polypeptide contains non-natural amino acid residues, present technologies may not permit the use of recombinant nucleic acid methodologies for the polypeptide preparation. Presently, protein expression from cloned genes is limited by the ability of a transfer ribonucleic acid molecule (tRNA) to carry amino acid residues into the enzyme complex responsible for protein synthesis. For these non-natural amino acids that are not recognized by a tRNA or by the enzymes involved in protein synthesis by a recombinant nucleic acid method, polypeptide synthesis is limited to synthetic means.

After a subject polypeptide has been prepared to contain a pair of coordinating amino acid residues, the polypeptide is admixed with an aqueous solution containing a metal cation as disclosed above for a metallopeptide in the form of a dissolved metal salt having the metal cation and an acceptable counter ion to form a biological reaction admixture. Acceptable counter ions are preferably monovalent, and have a dissociation constant relative to the cation that is biased in favor of dissolution and metallopeptide complex formation.

A biological reaction admixture contains the polypeptide and the metal cation in a ratio and at concentrations that favor complex formation. Typically, the peptide is present in the admixture at greater than 1 uM, and preferably greater than 10 uM. The metal cation is preferably present in at least one molar equivalent of the peptide, and more preferably in excess, such as greater than five molar equivalents to the peptide to assure rapid and complete metal-peptide complex formation. The biological reaction admixture can also contain solvent, buffers and other components, and has a pH such that the admixture is compatible with metal cation solubility and metal-peptide complex formation when maintained under biological reaction conditions.

The biological reaction admixture is then maintained under biological reaction conditions for a time period sufficient for the metal cation to complex with the polypeptide in the biological reaction admixture and form a composition containing a metallopeptide. Biological reaction conditions are temperature conditions that maintain solubility of the polypeptide and the free metal cation solution, and typically is from about 0 degrees C (0 C) to about 50 C, preferably 4 C to 40 C.

Metal cation complexation with ligands in a polypeptide's metal binding site typically proceeds at a rapid rate, and is essentially complete in the time required to thoroughly mix the solutions to form the biological reaction admixture. However, where the production of the metal cation having the appropriate oxidation step requires a slow reduction step, it is convenient to include in the biological reaction admixture reagents for reducing a metal ion precursor so that, once reduced, the reduced metal cation is available to react with (complex) the polypeptide. An example of this latter procedure is described in Example 2B, where the ruthenium- (III) complex is reduced over six hours by zinc amalgam in the same admixture for complexing the polypeptide.

Thus, in one embodiment the present invention provides for a method for preparing a metallopeptide having a stabilized secondary structure comprising the steps of:

(a) preparing a polypeptide having a preselected amino acid residue sequence, a portion of said sequence capable of forming a secondary structure having a hydrophilic region, wherein the polypeptide includes two coordinating amino acid residues that are aqueous solvent-accessible and that define a metal binding site in said hydrophilic region;

(b) admixing said polypeptide with a preselected metal cation in aqueous solution, said metal cation being capable of forming a metal polypeptide complex at said binding site by chemical bonds between the coordinating amino acid residues and metal to form a biological reaction admixture; and (c) maintaining said biological reaction admixture under biological reaction conditions for a time period sufficient for said metal cation to bind to said coordinating amino acid residues through said metal-ligand coordinating contacts and form a metallopeptide having a secondary structure stabilized by said bonded metal cation, i.e., a metallopeptide composition of this invention.

In another embodiment of a method to produce a stabilized metallopeptide, it is desirable to determine the preference of an engineered metal binding site for a particular metal cation. By determining the preference, an optimum metal cation peptide complex can be produced that yields a maximum degree of stabilization of the polypeptide's secondary structure.

The process for determining metal cation preferences by a particular polypeptide involves first preparing a series of biological reaction admixtures as before, each containing the polypeptide of interest and also containing a different metal cation. Thereafter, the admixtures are maintained as described before under biological reaction conditions so that the metal cation can complex with the polypeptide and form a metallopeptide.

Each of the series of maintained biological reaction admixtures is then individually evaluated (determined) (determined) for the presence of a stabilized secondary structure, and preferably for the amount (degree) of structure stabilization. The determination is typically conducted by measuring the amount of secondary structure present in a solution of peptide prior to admixture with a metal cation, and then measuring the amount of secondary structure present in the biological reaction admixture after the maintenance step. An increase in detectable secondary structure in the solution when comparing before and after admixture indicates that the metal cation has complexed with the metal binding site of the polypeptide and thereby stabilized the secondary structure contained therein.

Detecting changes (increases) in secondary structure of a polypeptide in solution can be conducted by a variety of assays known in the art, and include the optical measurement techniques of circular dichroism (CD), Roman spectrometry, and the physical measurement of susceptibility to heat denaturation. Exemplary methods for measuring circular dichroism and heat denaturation to characterize secondary structures are described in detail in Examples 3A and 3B.

By applying the step of determining the degree of secondary structure induced in a polypeptide by the admixture of a particular metal cation, and concurrently evaluating the results using several different metal cations, the preference of a metal binding site for the metal cation is determined. This process of screening several metal cations for their "preference" to bind a particular polypeptides metal binding site is demonstrated in Example 3A for peptides 1, 2, 4, 5, 6, and 12.

By the results described in Example 3A, it can be seen that for a particular polypeptide having an engineered metal binding site, one or more metal cations were identified that effectively stabilize the polypeptide and increase the content of secondary structure in the resulting metallopeptide. In addition, it is seen that for any particular metal binding site the most preferred metal cation may be different than the preferred cation for different metal binding site. Note, for example, that peptides 1 and 2 are stabilized preferentially by Cu(II) and Zu(II) [Example 3A(2)] peptides 4, 5, and 6 are stabilized preferentially by Ni(II) and peptide 12 is stabilized preferentially by Cu(II) [Example 3A(3)].

The invention therefor also contemplates a method for producing a stabilized metalloprotein by incorporating the aforementioned screening procedure to determine the preferred metal cation for complexing and stabilizing the secondary structure of a predetermined polypeptide. In this embodiment, the method comprises in addition to the first three steps (a), (b), and (c) above, the additional steps of:

(d) conducting steps (b) and (c) as before except including a metal cation different from the metal cation admixed in step (b);

(e) determining the amount of secondary structure exhibited by the polypeptide present in each of the maintained biological reaction admixtures formed in steps (c) and (d); and (f) selecting the maintained admixture that exhibits the greatest amount of secondary structure according to the determination of step (e) to form a metallopeptide having a stabilized secondary structure.

EXAMPLES

The following examples are given for illustrative purposes only and do not in any way limit the scope of the invention.

1. Synthetic Polypeptides

Synthetic polypeptides having amino acid residue sequences that correspond to the formulae shown in Table 2 were synthesized by the solid phase method using t-BOC chemistry according to published protocols. Barany, G., *The Peptides*, 2:3 (1979). The synthesized peptides were purified by reversed-phase $C_{18}$ HPLC.

TABLE 2

Synthetic Polypeptides

| Polypeptide Designation (SEQ ID No.)[1] | Amino Acid Residue Sequence |
|---|---|
| 1 | Ac-AEAAAKEAAAKCAAAHA-CONH$_2$ |
| 2 | Ac-AEAAAKEAAAKHAAAHA-CONH$_2$ |
| 3 | Ac-AEAAAKHAAAHEAAAKA-CONH$_2$ |
| 4 | Ac-AEAAAKEAAAKHAAAHA-CONH$_2$ |
| 5 | Ac-AEAAAKHAAAHEAAAKA-CONH$_2$ |
| 6 | Ac-AHAAAHEAAAKEAAAKA-CONH$_2$ |
| 7 | Ac-ACAAAHEAAAKEAAAKA-CONH$_2$ |
| 8 | Ac-AAHALEHQAKALKEAAQKA-CONH$_2$ |
| 9 | Ac-AACALEHQAKALKEAAQKA-CONH$_2$ |

TABLE 2-continued

Synthetic Polypeptides

| Polypeptide Designation (SEQ ID No.)[1] | Amino Acid Residue Sequence |
|---|---|
| 10 | Ac-AAHALECQAKALKEAAQKA-CONH$_2$ |
| 11 | Ac-AAJ$_1$ALEJ$_1$QAKALKEAAQKA-CONH$_2$ |
| 12 | Ac-AAJ$_2$ALEJ$_2$QAKALKEAAQKA-CONH$_2$ |

[1]All polypeptides referred to herein by polypeptide designation number, e.g., "peptide 1", are also referred to by sequence identification number e.g. "SEQ ID No. 1", and are further described the SEQUENCE LISTING portion of the Specification.

In Table 2, the following abbreviations are used to indicate chemical structures of the amino acid residue sequences:

Ac indicates an acetylated amino terminus.
CONH$_2$ indicates an amidated carboxyl terminus.
J$_1$ is represented by Xaa in the SEQUENCE LISTING at amino acid residue sequence positions 3 and 7 and indicates a non-natural amino acid having the structure:

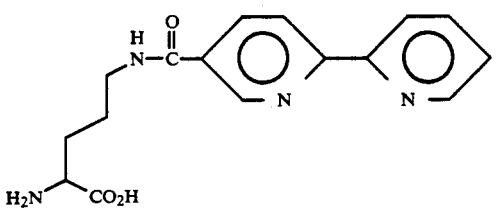

with the chemical formula: NH$_2$CH(R)—CO$_2$H, where R=(CH$_2$)$_n$—NHC(O)-4-[2,2'-bipyridine] and n=3.

J$_2$ is represented by Xaa in the SEQUENCE LISTING at amino acid residue sequence positions 3 and 7 and indicates a non-natural amino acid having the structure:

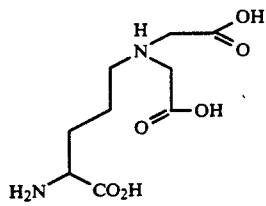

with the chemical formula: NH$_2$CH(R)—CO$_2$H, where R=(CH$_2$)$_n$N(CH$_2$CO$_2$H)$_2$ and n=3.

For the synthesis of peptides 11 and 12, having the non-natural amino acids J$_1$ and J$_2$, J$_1$ and J$_2$ were first prepared using conventional synthetic and well known methods and then were incorporated into the polypeptide as for a natural amino acid using the solid phase method.

2. Formation of Metallopeptide Complexes

A. Complexing Metal Ions with a Model Alpha Helix

Peptides 1 and 2 were prepared as in Example 1 and have a sequence shown in Table 2. The peptides were separately resuspended in either water or a solution of 10 mM sodium borate in the presence of 0.5 mM beta mercaptoethanol. The resuspended peptides were then admixed with solutions of commercially available salts to form the solutions described in Table 2 having the final concentrations of peptide and metal salt shown.

TABLE 3

Peptide Metal Salt Solution Admixtures

| Solution Number | Peptide | [Peptide][1] | Buffer[2] | (pH) | Metal | [Metal][3] |
|---|---|---|---|---|---|---|
| 1 | 1 | 5.9 | B | 8.0 | No salt | — |
| 2 | 1 | 5.9 | B | 8.0 | CdCl$_2$ | 1.0 |
| 3 | 1 | 5.9 | B | 8.0 | CdCl$_2$ | 2.5 |
| 4 | 1 | 5.9 | B | 8.0 | CdCl$_2$ | 4.0 |
| 5 | 1 | 5.9 | B | 8.0 | CdCl$_2$ | 5.6 |
| 6 | 1 | 5.9 | B | 8.0 | CdCl$_2$ | 15 |
| 7 | 1 | 2.2 | W | 6.65 | No salt | — |
| 8 | 1 | 2.2 | W | 6.65 | CdCl$_2$ | 73 |
| 9 | 1 | 5.9 | B | 8.0 | ZnCl$_2$ | 5.6 |
| 10 | 2 | 1.8 | B | 6.1 | No salt | — |
| 11 | 2 | 1.8 | B | 6.1 | CuSO$_4$ | 3.3 |
| 12 | 2 | 1.8 | B | 6.1 | CuSO$_4$ | 6.6 |
| 13 | 2 | 1.8 | B | 6.4 | CuSO$_4$ | 7.4 |
| 14 | 2 | 61 | B | 7.5 | CdCl$_2$ | 22 |
| 15 | 2 | 61 | B | 5.3 | CuCl$_2$ | 6.6 |
| 16 | 2 | 61 | B | 6.3 | NiCl$_2$ | 21 |
| 17 | 2 | 61 | B | 7.5 | ZnCl$_2$ | 7.5 |

[1]Peptide concentrations are expressed as × 10$^{-6}$M.
[2]B indicates sodium borate, W indicates water.
[3]Metal salt concentrations are expressed as × 10$^{-5}$M.

Nuclear magnetic resonance (NMR), absorption spectra and circular dichroism analyses were performed on the above admixtures to evaluate the effects of the admixed metal ions on stability of any alpha helix present in the admixed peptide. The results of these experiments are described below and in Example 3.

Figure 1:
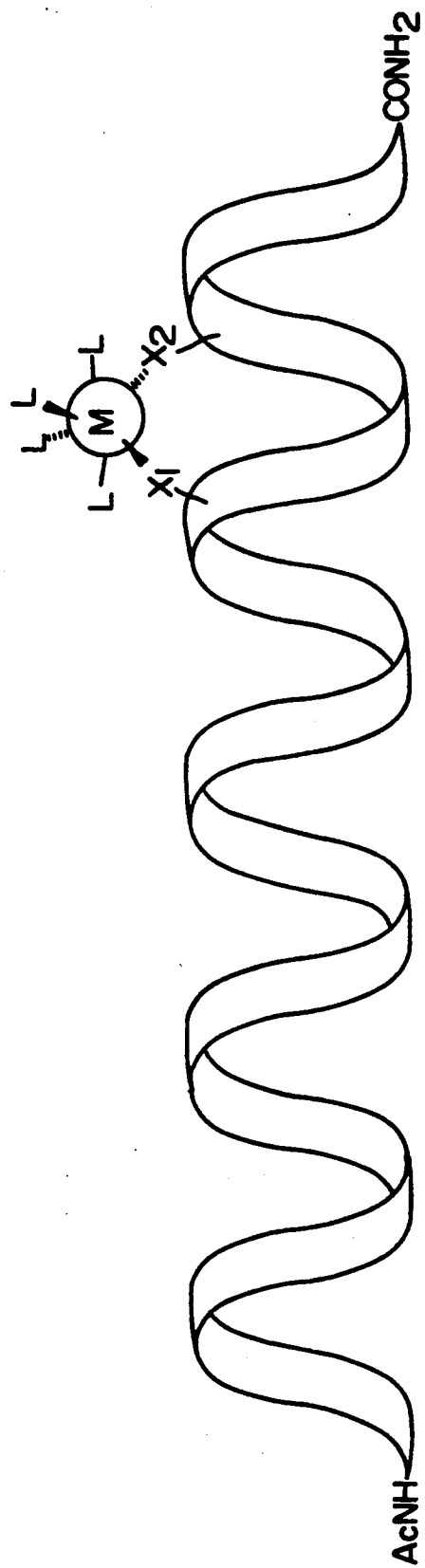
FIG. 1 shows a helix ribbon diagram illustrating metal ion complexation to the side chain of amino acid residues in the i and i+4 positions of an alpha-helix. The N-terminus, designated AcNH, is an acetylated amide. The carboxy terminus, designated $CONH_2$, is an amidated carboxyl. The metal ion binding site in the, amino acid residue sequence is designated by $X_1$ and $X_2$ where peptide 1 (Table 2) has cysteine and histidine residues in those locations, respectively, and where peptide 2 (Table 2) has two histidine residues at those positions.

A schematic representation of a synthetic peptide in an alpha helical conformation is shown in FIG. 1. The alpha helix is stabilized by metal ion complexation to the side chain of the coordinating amino acid residues shown at positions i and i+4. These positions are labeled X$_1$ and X$_2$, respectively, in the amino acid residue sequence shown in the figure. In peptide 1, X$_1$ and X$_2$ are cysteine and histidine residues, respectively. In peptide 2, histidine residues occupy both positions.

B. Forming an Exchange-Inert Metallopeptide Complex Using a Ruthenium Compound Cis-[Ru(NH$_3$)$_4$Cl$_2$]Cl was prepared according to published procedures. Pell et al., Inorg. Synthesis, 26:25 (1989). A solution of cis-[Ru(NH$_3$)$_4$Cl$_2$]Cl was then prepared in degassed 50 mM Tris buffer, pH 7.0, and the ruthenium complex in the solution was reduced in the presence of zinc amalgam to form cis-[Ru(NH$_3$)$_4$(H$_2$O)$_2$]$^{2+}$.

A solution containing peptide 2, prepared as in Example 1, in degassed 50 mM Tris buffer, pH 7.1 was admixed with cis-[Ru(NH$_3$)$_4$(H$_2$O)$_2$]$^{2+}$ to form a biological reaction admixture with 10 uM peptide and 50 uM ruthenium complex. The biological reaction admixture was maintained at room temperature for 6 hours, and then air oxidized to form a ruthenium-peptide 2 complex, also referred to generally as a Ru(III)-peptide complex. The complex was then purified using cation exchange chromatography on a BioRex-70 column (BioRad Laboratories, Richmond, Calif.) to form a composition containing the purified ruthenium-peptide 2 complex, i.e., an isolated metallopeptide.

A compostion containing a ruthenium-peptide 3 complex was similarly prepared by using peptide 3, prepared as in Example 1, in place of peptide 2 in the above procedures.

The resulting purified ruthenium-peptide complex containing compositions formed using peptide 2 or peptide 3 were characterized as being greater than 98% pure when analysed on analytical reverse phase chromatography using a $C_{18}$ polysulfoethyl aspartamide RP-HPLC column, or when analysed on a BioRex-70 cation exchange column. For both compositions, the total ruthenium content was analysed by atomic absorption spectroscopy and exhibited 1:1 Ru:peptide stoichiometry (±15%). Additionally, both Ru(III)-complexed peptides exhibited the characteristic amino acid analysis patterns and peak heights except for the histidine peaks which were on average 70% smaller than expected indicating that the histidine residues were specifically modified. FAB MS of both complexed peptides exhibited the expected molecular weight ion (M/Z=1797) as well as a prominent peak at 1729 corresponding to the loss of four $NH_3$ ligands.

C. NMR Identification of Metallopeptide Complex Formation

The $Cd^{2+}$ or $Zn^{2+}$ ion-containing peptide metal salt solution admixtures prepared in Example 2A were subjected to NMR to identify metallopeptide complex ligands. The results of NMR studies show that both of histidine 2H and 4H resonances in peptide 2 (2.5 mM in $D_2O$, pH 6.6) occurring at $\delta 7.87$, 7.74, and $\delta 6.89$, 6.87 shift upfield, upon addition of $Zn^{2+}$, to $\delta 7.75$, 7.71, and $\delta 6.87$, 6.67, respectively. Similar results are obtained for peptide 1 (2.5 mM in $D_2O$, pH 6.5) in the absence ($\delta 7.91$ and 6.95) and the presence of $Cd^{2+}$ ($\delta 7.71$ and 6.91). Of the 17 backbone amide protons in peptide 1 (3.0 mM, $CdCl_2$ 0.3M in $H_2O$, pH 5.1) 11 have been sequentially assigned using COSY and NOESY spectra. Amide resonances for N-terminal amino acid residues of peptide 1 exhibit $^3J_{HN\alpha} < 5$ Hz, which is further evidence that helical structure extends to the N-terminus.

The Ru(III)-peptide 3 complex prepared in Example 2B was subjected to NMR spectroscopy to evaluate the chemoselective functionalization of the peptide's histidine residues by the metal salt. The results of these studies show that the histidine C-2 and C-4 protons of peptide 3 occurring at $\delta 8.52$, 8.51 and 7.2.0, 7.19 undergo dramatic upfield shifts to $\delta 7.47$, 7.15 and 6.98, 6.83, respectively, upon attachment to the tetraamineruthenium(II) moiety. Additionally, the histidine signals in the Ru(III)-peptide 3 complex, formed upon oxidation, display paramagnetic shifting and appear as broad peaks at $\delta 0.56$ and $-0.78$.

These studies confirm that metal salts interact with histidine residues on synthetic peptides to form macrocyclic bidentate complexes which are exchange-inert over the time for making NMR measurements.

D. Absorption Spectroscopy to Identify Metallopeptide Complexes

The Ru(III)-peptide 2 complex prepared in Example 2B was subjected to absorption spectroscopy to further confirms the formation of a metallopeptide complex.

Figure 2:
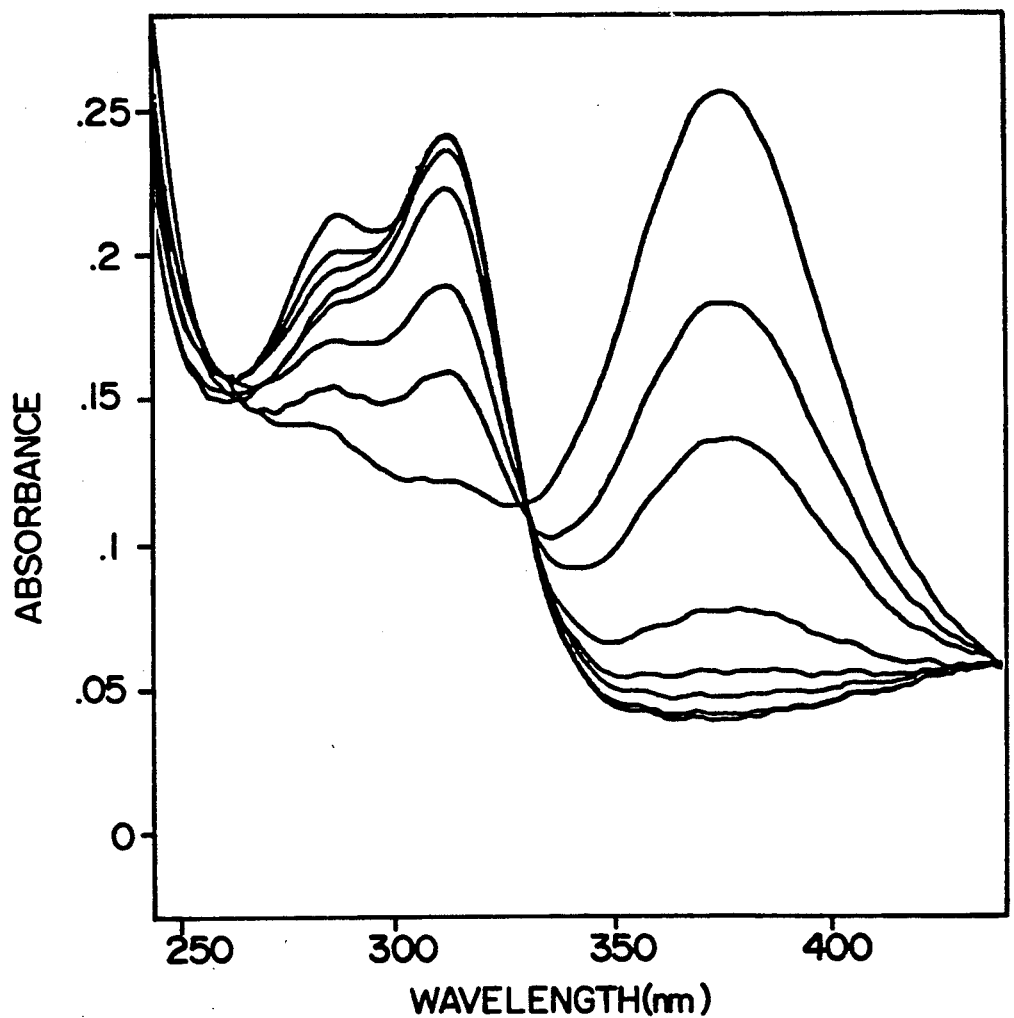
FIG. 2 illustrates the absorption spectra of a tetraamine ruthenium(III)-peptide 2 complex with absorbance plotted against wavelength in nanometers (nm) when measured as described in Example 2D. As the pH of the complex is shifted from acidic to alkaline, the spectra maxima change. Complex at a pH of 4.7 exhibits an absorption maximum at 313 nm and at a pH of 7.9 exhibits a maximum at 376nm. The curves in between represent pH values of 5.5, 6.1, 6.6, 7.1, and 7.5.

The results of the absorption spectroscopic analysis are presented in FIG. 2, and show that the absorption spectrum of the Ru(III) complex of peptide 2 exhibits ligand to metal charge transfer bands at 287 nm and 313 nm below pH 6.5 which shift to 376 nm above pH 8 with an isosbestic point at 331 nm.

Absorption spectra analysis of Ru(III)-peptide 3 complex prepared in Example 2B exhibited similar UV spectra and pH profile when analysed by absorption spectroscopy. The pronounced shift in absorption maxima with increasing pH is consistent with the behavior of the Ru(III) ions containing coordinated imidazoles and is attributed to N-H deprotonation at the "pyrrole nitrogen", Sunberg et al., *J. Am. Chem. Soc.*, 96:381 (1974). The absorption data give a $pK_a$ value of 7.5 for the imidazole N-H of the coordinated histidine which is 7 orders of magnitude lower than the $pK_a$ of uncomplexed histidine. The spectral similarity with the simple ruthenium(III)-imidazole complexes and the characteristically facile metal-ion promoted imidazole N-H ionization further support the formation of the metallopeptide complex.

3. Stabilization of Protein Secondary Structure

A. Circular Dichroism (CD) to Measure Degree of Stability (1) CD of Peptides 1 and 2 in the Presence of Metal Ions Peptide metal salt solution admixtures prepared in Example 2A were subjected to CD analyses according to published procedures to measure the degree of stability induced by metal ion complexation with peptides, Greenfield et al., *Biochem.*, 8:4108 (1969) and Johnson, *Ann. Rev. Biophys. Chem.*, 17:145 (1988). All CD data reported herein have an uncertainty of ±2–5% for a 100% helix, $[\Theta]_{222} = -35,000$, and are based on several CD measurements of both peptides 1 and 2 in the presence and absence of metal ions in various $TFE/H_2O$ mixtures at $-10$ to 20C. The results of these analyses are shown in FIG. 3.

Panel A of FIG. 3 shows the CD spectrum of Peptide 1 at 20 C and in the presence of increasing amounts of $CdCl_2$. In this study, solutions 2, 3, 4 and 6 of Table 3 were compared to a solution containing peptide 1 in the absence of $CdCl_2$. The curves shown from the top (arrow) to the bottom represent the data collected using increasing concentrations of $CdCl_2$.

Figure 3A:
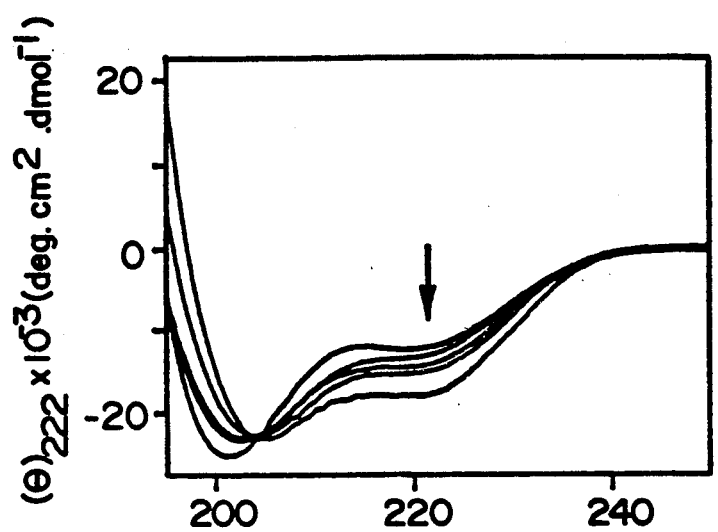
FIGS. 3A, 3B and 3C illustrate the circular dichroism (CD) spectra of separate solutions of peptides in the presence of metal ion salt solutions measured as described in Example 3A(1). The CD spectrum is plotted against increasing wavelength. In panel 3A, the CD spectrum of peptide 1 ($5.9 \times 10^{-6}$M in 10 mM sodium borate, 0.5 mM mercaptoethanol, pH 8.0, 21° C.) in the presence of increasing amounts of $CdCl_2$ is shown. From the top curve (arrow) to the bottom curve, the $Cd^{2+}$ concentrations shown include 0, $1.0 \times 10^{-5}$, $2.5 \times 10^{-5}$, $4.0 \times 10^{-5}$, and $1.5 \times 10^{-4}$M, respectively. The decrease in the CD spectrum reflects the increased stability of the peptide alpha-helical conformation by increased metal ion concentrations.
Figure 3B:
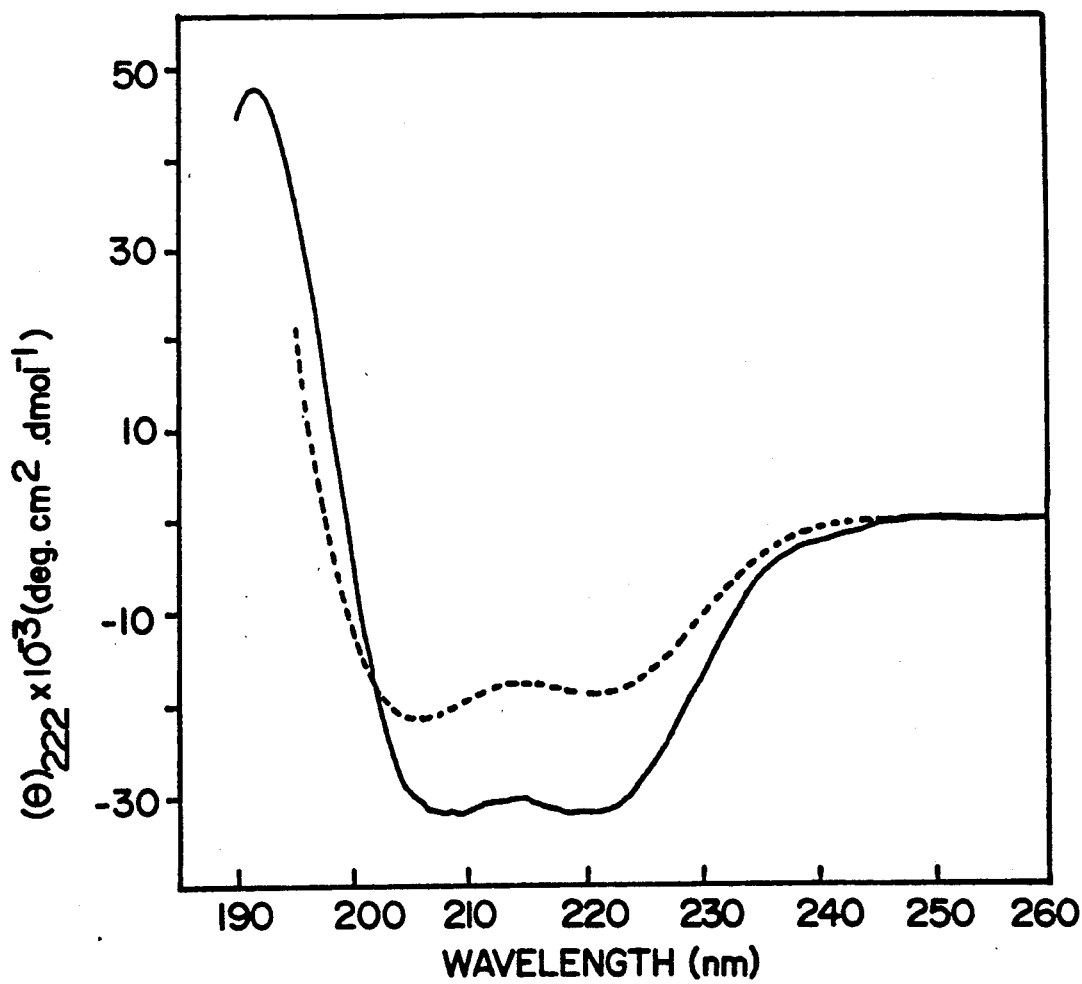

The results of CD analysis of peptide 1 admixed with increasing amounts of $CdCl_2$ show an enhancement in the helix content of the peptide by the increase in the 222 nm minima (FIG. 3A). An isodichroic point occurs at 204 nm which is characteristic of helix-coil transition.

CD spectrum analysis of peptide 1 in solution 8 (Table 3) containing $CdCl_2$ was compared to solution 7 without $CdCl_2$ at 4 C. The results of the CD spectrum analysis shown in FIG. 3B (solid curve) indicate that the interaction of cadmium ion with histidine and cysteine side chains at the 16th and 12th amino acid residue positions, respectively (Table 1), provides sufficient stabilization energy to induce up to 90% alpha-helicity ($[\Theta]_{222} = -31,500$) at 4C. In contrast, peptide 1 in the absence of metal ion (solution 7) exhibits 54% alpha helicity ($[\Theta]_{222} = 18,800$) at 4C (dotted curve).

Figure 3C:
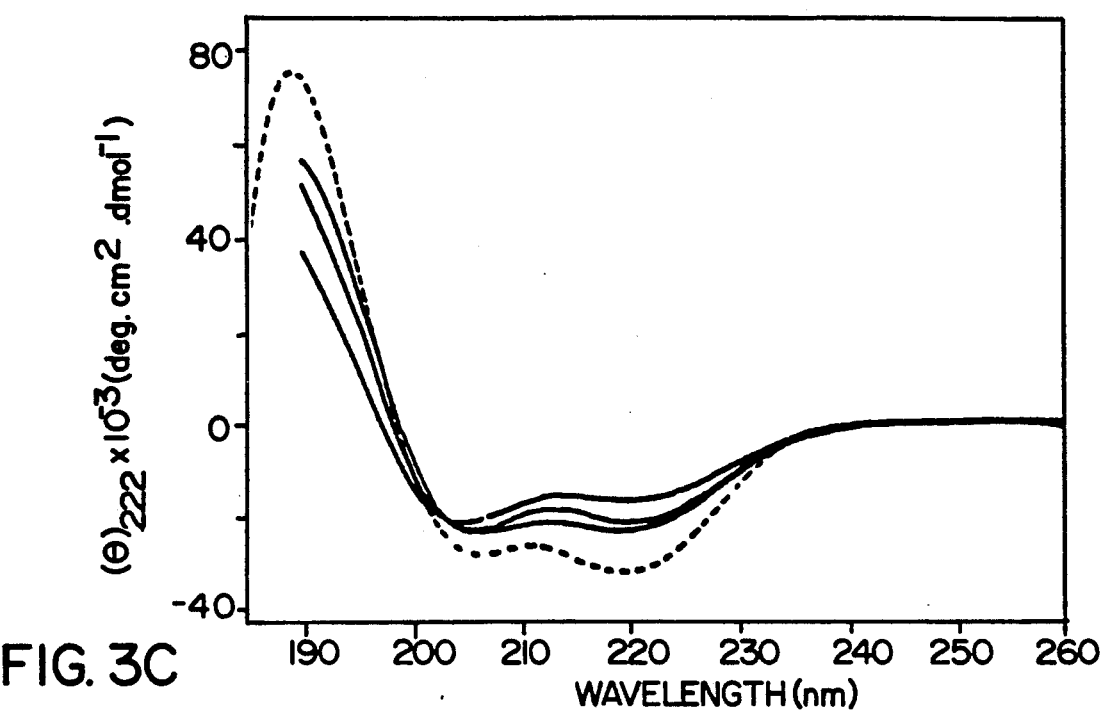

Similar studies were performed with peptide 2, which has histidine residues at both positions 12 and 16 (Table 2), in admixtures with various metal ion salt solutions (Table 3). Solutions of peptide 2 in the presence of increasing concentrations of $CuSO_4$ (solutions 11, 12 and 13) were compared with solutions of peptide lacking $CuSO_4$ at 21 C. These results are represented in FIG. 3C by the solid curves as in FIG. 3A. Solution 13 containing peptide 2 and $CuSO_4$ was also tested at 0 C. The CD spectral pattern of solution 13 is seen in the dashed curve of FIG. 3C.

The results of the CD spectral analyses show that peptide 2 having a pair of histidine residues at the relative positions of i and i+4 displays about 90% alpha-helicity ($[\Theta]_{222} = -31,100$) in the presence of $Cu^{2+}$ ions at 0 C. The alpha-helical stabilization was slightly enhanced in peptide metal ion solutions maintained at 0 C compared to those at 21 C.

The side chains of histidine and cysteine residues in positions i and i+4 of a peptide, thus can interact with transition metal ions to form a bidentate complex and concurrently fix the peptide backbone in an alpha-helical conformation. In this way, peptides of up to 75% alpha-helicity in water at room temperature and 90% alpha-helicity at 0-4 C are obtained.

(2) Metal Ion Selectivity and Affinities of Peptides 1 and 2

Metal ion selectivity is an expected consequence of site specific metal-ligand interaction. The extent of helical induction, to a first approximation, depends on the affinity of metal ion toward the ligands employed, and on the compatibility of metal ion geometry and coordination sphere with the alpha-helical conformation. Thus, although numerous metal cations may induce and stabilize alpha helix formation, the metal ion having the greatest relative affinity for the ligands employed is preferred and can readily be determined.

To determine the relative affinities of the different metal ions, $CdCl_2$, $CuCl_2$, $NiCl_2$, and $ZnCl_2$, for complexing with the ligands of peptides 1 and 2, the solutions 5, 9, and 14-17 prepared in Example 2B, were subjected to CD analyses as described above.

The results of this analysis are shown in FIG. 4. Both $Cu^{2+}$ and $Zn^{2+}$ bind peptide 2 with similar affinities and increase the helical content to the same extent. On the other hand, $Ni^{2+}$ exhibits a similar binding constant with respect to $Cd^{2+}$ but shows higher helical induction. While peptide 2 displays considerable helical induction in the presence of $Zn^{2+}$, peptide 1 is $Cd^{2+}$ selective and addition of Zn2+ has no effect on the helical content. In addition, helicity is independent of concentration of added NaF up to 250 mM for both peptide 1 (2.5 uM in 5 mM sodium borate, pH 8.0) and peptide 2 (2.0 uM in 5 mM sodium borate, pH 6.1). Peptides 1 and 2 show CD spectra independent of the peptide concentration in the presence and the absence of metal ions in the measured range of 0.5-70 uM, consistent with intramolecular helical structures. Nonligated metal coordination sites are most likely occupied by water molecules and addition of external ligands such as 5-nitro-1,10-phenanthroline or mercaptoethanol does not affect the stability of the helical conformation.

(3) Metal Ion Selectivity and Affinities of Other Peptides

Peptides, prepared in Example 1, and admixed with various metal salt solutions as described in Example 2B, were subjected to CD analysis to characterize metal ion selectivity with respect to the position of the metal binding site in the alpha-helical sequence.

The results of this study indicate that peptide 4 binds $Ni^{2+}$, $Cd^{2+}$, $Cu^{2+}$ and $Zn^{2+}$ in descending order of affinity with $Cu^{2+}$ and $Zn^{2+}$ being nearly equivalent. Peptide 5 binds $Ni^{2+}$ and $Cu^{2+}$ predominantly followed by $Cd^{2+}$ then $Zn^{2+}$. Peptide 6 binds $Ni^{2+}$ and $Cu^{2+}$ in descending order of affinity and exhibits no significant binding of either $Cd^{2+}$ or $Zn^{2+}$. Peptide 12 binds $Cu^{2+}$, $Hg^{2+}$, $Cd^{2+}$, $Fe^{2+}$, $Zn^{2+}$ and $Pb^{2+}$ in descending order of affinity at a pH of 6.0, with $Zn^{2+}$ and $Pb^{2+}$ being equivalent.

The affinity of metal ions for binding sites on alpha-helical peptides is influenced by the sequence position of the amino acids to which they bind. The residues, separated by three amino acids, bind $Ni^{2+}$ with the greatest affinity independent of position in the sequence, N-terminal, middle or C-terminal. $Zn^{2+}$ is the least effective in binding to the residue in all three positions.

$Cu^{2+}$ and $Cd^{2+}$ demonstrate variable affinities dependent on the position of the amino acid residues that contain the binding site. In peptide 12, a non-natural amino acid having a diacetato amino moiety at the side chain terminus has been inserted in positions 3 and 7. $Cu^{2+}$ binds to this moiety with a greater affinity than $Hg^{2+}$, $Cd^{2+}$, $Fe^{2+}$, $Zn^{2+}$ or $Pb^{2+}$. The binding of $Cu^{2+}$ to this non-natural amino acid residue results in the greatest stabilization of alpha-helical conformation observed to date. At 0° C. using $Cu^{2+}$ the helicity was about 100% ($\Theta=35,600$), and at 20° C. using $Cu^{2+}$ the helicity was about 80% ($\Theta=29,300$). The above studies indicate that unprecedented levels of helicity can be induced in short monomeric peptides by taking advantage of selective metal ion complexation.

(4) CD of Ru(III)-Peptide Complexes

Ru(III)-peptide complexes prepared in Example 2B were subjected to CD analysis to measure the alpha-helical stabilizing effect of ruthenium ions on peptides 2 and 3. The analysis was performed as described above. The results of the CD spectral measurements are shown in FIG. 5.

The results show that restriction of the conformational fluxionality of peptides 2 and 3 by the formation of an exchange-inert macrocyclic Ru(III) complex affords remarkably stable alpha-helical metallopeptides. The analysis of CD spectra of Ru(III) complexed peptides 2 and 3 at room temperature in water indicates >80% ($\Theta_{222}=-28,000$) and 50% ($\Theta_{222}=17,300$) alpha-helicity, respectively. In contrast, the free peptide 2 under similar condition is 45% helical ($\Theta_{222}=-16,600$) while uncomplexed peptide 3 exhibits CD spectrum of a random coil structure. The Ru(III) complexes exhibited CD spectra independent of peptide concentration in the measured range of 0.5 to 300 uM, and were monomeric complexes in solution.

B. Heat Denaturation Assay to Measure Melting Temperatures

In order to assess differences in helix stability between the metal ion complexed and uncomplexed forms of peptides 2 and 3, the conformational stability of each peptide in the presence and absence of transition metal ions was determined from heat denaturation studies according to published procedures. Pace et al., *In Protein Structure*, p. 311., IRL Press, (1989). The analysis of the thermal denaturation curves afforded linear G vs. T and van't Hoff plots; The data indicate that the formation of the exchange-inert Ru(III) complex contributes up to 1 kcal/mol toward the stability of the alpha-helical conformation and dramatically increase the melting temperature of both peptides by about 25 C. Complexed peptides 2 and 3 exhibit melting temperatures (Tm) of 35 C and 9.5 C, respectively, while the corresponding free peptides have $T_m$ values of 11 C and −15.5 C.

The above studies unequivocally establish that exchange-inert metal complexes can be effectively exploited in designing highly stable alpha-helical metallopeptides. The availability of a simple methodology for the formation of stable alpha-helical peptides can have considerable utility in the de novo design of biologically active peptides.

The present invention provides several advantages and benefits that involve the effect on a polypeptide or protein's biological properties as a result of stabilizing a secondary structure within a polypeptide chain by the teachings of the invention.

One advantage is provided by the increased thermostability of the polypeptide in a metallopeptide composition of this invention. Temperature lability is a major cause of loss of activity by enzymes and other proteins. Thus increasing thermostability will prolong the half life of an enzyme in bioreactors and in high temperature reactors. Exemplary enzymes particularly preferred for stabilization and having candidate secondary structures are high temperature thermostable DNA dependent DNA polymerases, staphylococcaL nuclease, ribonucleases, and the like thermostabilized metalloproteins.

Another advantage is to increase the half life of a polypeptide or protein in a hostile biological environment where degradation is due to protease activity such as for therapeutic proteins administered in the blood, and in bioreactions having protease activity. The stabilization of secondary structure lowers susceptibility to proteolytic degradation. Thus the invention contemplates a metallopeptide composition having increased resistance to proteolytic degradation, including therapeutic metallopeptides.

Insofar as biological function and biological activity, depends on the structure (conformation) of a polypeptide in either proteins or peptides (e.g., peptide hormones), an additional advantage of the invention is to increase the biological activity of the polypeptide by stabilizing the structure into a biologically active conformation. This advantage is particularly applicable to smaller polypeptides which are more likely to exhibit random coil structures.

Additional advantages are apparent to those skilled in the art of protein biochemistry and protein stabilization.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A metallopeptide comprising a polypeptide bonded to a metal cation at two coordinating amino acid residues that are aqueous solvent-accessible, said metallopeptide having a secondary structure stabilized by said bonded metal cation.

2. The metallopeptide of claim 1 wherein said secondary structure is an alpha helix and said coordinating amino acid residues are located at relative amino acid positions of i and i+4 on the polypeptide.

3. The metallopeptide of claim 1 wherein said secondary structure is a beta sheet having a beta turn and said coordinating amino acid residues are located at relative amino acid positions of i and i+3 on the polypeptide.

4. The metallopeptide of claim 1 wherein said secondary structure is a beta sheet having a beta turn and said coordinating amino acid residues are located at relative amino acid positions of i−1 and i+5 on the polypeptide.

5. The metallopeptide of claim 1 wherein said coordinating amino acid residues are selected from the group consisting of histidine, cysteine and methionine.

6. The metallopeptide of claim 1 wherein said coordinating amino acid residues are both histidine.

7. The metallopeptide of claim 1 wherein said coordinating amino acid residues are individually monodentate or bidentate with said metal cation.

8. The metallopeptide of claim 1 wherein one of said coordinating amino acid residues has a structure according to the formula:

$HO_2C-CH(R)-NH_2$;

where $R=(CH_2)_n-N(CH_2CO_2H)_2$ and n=1,2,3 or 4.

9. The metallopeptide of claim 1 wherein one of said coordinating amino acid residues has a structure according to the formula:

$HO_2C-CH(R)-NH_2$;

where $R=(CH_2)_n-HN-C(O)-4-[2,2'-bipyridyl]$ and n=1, 2 or 3.

10. The metallopeptide of claim 1 wherein one of said coordinating amino acid residues has a structure according to the formula:

$HO_2C-CH(R)-NH_2$;

where $R=(CH_2)_n NH-C(O)-5-[1,10-phenanthroline]$ and n=1, 2 or 3.

11. The metallopeptide of claim 1 wherein said metal cation is selected from the group consisting of Zn(II), Cd(II), Cu(I), Cu(II), Ni(II), Ru(II), Ru(III), Pt(II), Pd(II), Co(II), Co(III), Mg(II), Ba(II), Sr(II), Fe(II), Fe(III), V(III), Cr(II), Cr(III), Mn(II), Rh(III), Ag(I), Hg(II), Mo(III), Mo(IV), Mo(V), Mo(VI), W(III), W(IV), W(V), W(VI), Ca(II), Pb(II), Ce(III), Al(III), and Th(IV).

12. The metallopeptide of claim 1 wherein said metal cation forms a substantially exchange-inert complex with said polypeptide.

13. The metallopeptide of claim 1 wherein said metal cation forms an exchange-inert complex with said polypeptide having formula: cis-[Ru(NH3)4(L)(L')]3+, cis-Ru(ethylenediamine)2(L)(L')]3+, cis-Ru(triethylenetetraamine)(L)(L')]3+, cis-[Ru(2,2'-bipyridine)2(L)(L')]2+ or cis-[Ru(2,2'-bipyridine)2(L)(L')]3+, wherein L and L' are said coordinating amino acid residues of said polypeptide.

14. A metallopeptide composition having a stabilized secondary structure comprising:
(a) a polypeptide having an amino acid residue sequence, a portion of said sequence forming a secondary structure having a hydrophilic region, said hydrophilic region including two coordinating amino acid residues for binding a metal; and
(b) a metal cation bonded to the coordinating amino acid residues through at least one and not more than four metal-ligand coordination contacts with each of said coordinating amino acid residues.

15. The metallopeptide composition of claim 1 wherein one of said coordinating amino acid residues is monodentate and a second coordinating residue is bidentate with said metal cation.

* * * * *